US009085604B2

(12) United States Patent
Keay et al.

(10) Patent No.: US 9,085,604 B2
(45) Date of Patent: *Jul. 21, 2015

(54) ANTIPROLIFERATIVE FACTOR AND METHODS OF USE

(75) Inventors: Susan K. Keay, Ellicott City, MD (US); Christopher Michejda, North Potomac, MD (US); Maria Michejda, legal representative, North Potomac, MD (US); Zoltan Szekely, Gaithersburg, MD (US); Thomas Conrads, Pittsburgh, PA (US); Timothy Veenstra, Jefferson, MD (US)

(73) Assignees: University of Maryland, Baltimore, Baltimore, MD (US); The United States of America as represented by the Secretary of the Department of Health and Human Services, Bethesda, MD (US); The United Sates of America as Represented by the Department of Veterans Affairs, Washington, DC (US)

( * ) Notice: Subject to any disclaimer, the term of this patent is extended or adjusted under 35 U.S.C. 154(b) by 804 days.

This patent is subject to a terminal disclaimer.

(21) Appl. No.: 11/955,755

(22) Filed: Dec. 13, 2007

(65) Prior Publication Data

US 2009/0148505 A1 Jun. 11, 2009

Related U.S. Application Data

(63) Continuation-in-part of application No. 11/743,865, filed on May 3, 2007, now Pat. No. 8,680,056, which is a continuation of application No. 10/882,586, filed on Jul. 1, 2004, now abandoned.

(60) Provisional application No. 60/569,363, filed on May 8, 2004, provisional application No. 60/515,850, filed on Oct. 30, 2003, provisional application No. 60/484,010, filed on Jul. 1, 2003.

(51) Int. Cl.
*C07K 9/00* (2006.01)
*A61K 38/00* (2006.01)

(52) U.S. Cl.
CPC *C07K 9/005* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,523,290 A | | 6/1996 | LeBoeuf et al. |
| 5,811,393 A | | 9/1998 | Klagsbrun et al. |
| 5,916,871 A | | 6/1999 | Johnson |
| 5,962,645 A | * | 10/1999 | Keay et al. ............ 530/350 |
| 6,156,522 A | | 12/2000 | Keay et al. |
| 6,232,289 B1 | | 5/2001 | Keay et al. |
| 6,376,197 B1 | | 4/2002 | Keay et al. |
| 2002/0016443 A1 | | 2/2002 | Keay et al. ............ 530/350 |

FOREIGN PATENT DOCUMENTS

| | | | |
|---|---|---|---|
| WO | 2005/016248 | * | 2/2005 |
| WO | 2008/014484 | * | 1/2008 |
| WO | WO-2008/014484 A1 | | 1/2008 |
| WO | 2008/144485 | * | 11/2008 |

OTHER PUBLICATIONS

Keay, S.K., et al, Proceedings of the National Academy of Sciences, USA, 101(32): 11803-11808, 2004.*
Examiner's First Report on Patent Application No. 2004264853 issued Jan. 14, 2010 during prosecution of corresponding Australian Patent Application No. 2004264853.
Regan et al., "Heme Oxygenase-1 Induction Protects Murine Cortical Astrocytes From Hemoglobin Toxicity," Neurosci Lett. Mar. 17, 2000; 282(1-2):1-4.
Kim, Jayoung, et al; "p53 Mediates Interstitial Cystitis Antiproliferative Factor (APF)-Induced Growth Inhibition of Human Urothelial Cells"; FEBS Letters, 2007, vol. 581, pp. 3795-3799.
Hsieh et al., "Biochemical characterization of Wnt-Frizzled interactions using a soluble, biologically active vertebrate Wnt protein," Proc. Natl. Acad. Sci. USA, 96:3546-3551, 1999.
Kaczmarek et al., "Structure-activity relationship studies for the peptide portion of the bladder epithelial cell antiproliferative factor from interstitial cystitis patients," J Med Chem., 51(19):5974-5983, 2008.
PCT International Search Report and Written Opinion issued in International Application No. PCT/US2010/045863, mailed Dec. 14, 2010.
Japanese Office Action, issued Mar. 12, 2010 (published Mar. 12, 2010) during the prosecution of Japanese Application No. 2006-517828.
Saitoh et al., "Molecular cloning and characterization of human Frizzled-8 gene on chromosome 10p11.2." Int J Oncol. May 2001;18(5):991-6.
Supplemental European Search Report issued during the prosecution of European Application No. 04777402, Feb. 21, 2008.
Keay et al., "Normalization of Proliferation and Paracellular Permeability of Bladder Epithelial Cells From Interstitial Cystitis Patients by a Synthetic Inhibitor of Antiproliferative Factor," Abstract. The FASEB Journal. 2008;22:1120.9.
Campbell et al. (Laboratory Techniques in Biochemistry and Molecular Biology .1986 vol. 13, p. 1-32).
Auger, G. et al; Purification and Partial Characterization of a Hepatocyte Antiproliferative, Glycopeptide, Journal of Cellular Biochemistry, (1989) vol. 40, pp. 439-451.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression associated with interstitial cystitis or antiproliferative factor treatment, Physiol. Genomics (2003) vol. 14, pp. 107-115.

(Continued)

*Primary Examiner* — Sheela J Huff
(74) *Attorney, Agent, or Firm* — Norton Rose Fulbright US LLP

(57) ABSTRACT

A novel antiproliferative factor comprising a glycopeptide is disclosed. In specific embodiments, the novel antiproliferative factor is associated with the bladder. Compositions, diagnostic kits and reagents, and methods of using the compounds for identifying and/or treating interstitial cystitis and cancer are disclosed.

26 Claims, 12 Drawing Sheets

(56) References Cited

OTHER PUBLICATIONS

Keay, S., et al.; Current and future directions in diagnostic markers in interstitial cystitis, Intern'l J. of Urology (2003) vol. 10, pp. S27-S230.

Keay, S., et al.; Decreased In Vitro Proliferation of Bladder Epithelial Cells from Patients with Interstitial Cystitis, The Journal of Urology (2003) vol. 61, pp. 1278-1284.

Rashid, H., et al; Interstitial cystitis antiproliferative factor (APF) as a cell-cycle modulator, BMC Urology (2004) 4:3, pp. 1-5.

Zhang, C., et al; Comparison of APF Activity and Epithelial Growth Factor Levels in Urine from Chinese, African-American, and White American Patients with Intestitial Cystitis, Urology (2003) vol. 61, pp. 897-901.

Parson, C.L., et al., "Role of Toxic Urine in Interstitial Cystitis", Journal of Urology (1990) vol. 143, p. 373A.

Beier-Holgersen, R., "The in vitro cytotoxicity of urine from patients with interstitial cystitis", Journal of Urology (Jan. 1994), vol. 151, pp. 206-207.

Janeway et al. (Immobiology 1997, Section 2-7).

Keay et al. Urology 2001, vol. 57, p. 9.

* cited by examiner

ANTIPROLIFERATIVE FACTOR AND METHODS OF USE

STATEMENT REGARDING FEDERALLY SPONSORED RESEARCH OR DEVELOPMENT

The present invention was generated at least in part with funds from National Institutes of Health NIH, NIDDK DK52596; the Veterans Administration (VA Merit Review Funding); and intramural National Cancer Institute funds. The United States Government has certain rights in the invention.

This application is a continuation-in-part patent application that claims priority to U.S. patent application Ser. No. 11/743,865, filed May 3, 2007, which claims priority to U.S. patent application Ser. No. 10/882,586, filed Jul. 1, 2004, which claims priority to U.S. Provisional Patent Application Ser. No. 60/484,010, filed Jul. 1, 2003; U.S. Provisional Patent Application Ser. No. 60/515,850, filed Oct. 30, 2003; U.S. Provisional Patent Application Ser. No. 60/569,363, filed May 7, 2004, all of which are incorporated by reference herein in their entirety.

FIELD OF THE INVENTION

The present invention is directed to fields of medicine, biochemistry, cell biology, and chemistry. More specifically, the present invention addresses a novel compound and derivatives thereof having growth inhibitory activity. The present invention is further directed to uses of the novel compounds and derivatives thereof as a biomarker and/or a diagnostic for bladder disorders, particularly interstitial cystitis. The present invention also relates to the treatment of any disease involving uncontrolled cell proliferation, such as cancer.

BACKGROUND OF THE INVENTION

Approximately one million people in the United States suffer from the bladder disorder interstitial cystitis, which is a chronic painful urinary bladder condition characterized by thinning or ulceration of the bladder epithelial lining (Curhan et al., 1999).

Cystoscopic abnormalities seen in the bladder of patients with this disorder include petechial hemorrhages called "glomerulations" and ulcers that extend into the lamina propria (Hunner's ulcers) (Johansson and Fall, 1990; Skoluda et al., 1974). The most consistent histologic abnormalities include denudation or thinning of the bladder epithelium to 1-2 cell layers (Johansson and Fall, 1990; Skoluda et al., 1974; Tomaszewski et al., 2001). These findings suggest that interstitial cystitis may be caused by an inhibition of normal bladder epithelial cell proliferation, resulting in a loss of epithelial barrier integrity with subsequent exposure of sensory nerve cells in the bladder wall to urinary constituents. However, the pathogenesis of interstitial cystitis is heretofore unknown.

The isolation of an antiproliferative factor ("APF") peptide that is made uniquely by bladder epithelial cells from interstitial cystitis patients (Keay et al., 2001; Keay et al., 2000) and profoundly inhibits normal bladder epithelial cell growth (Keay et al., 2003) was previously described. U.S. Pat. No. 5,962,645, incorporated by reference herein in its entirety, teaches a purified human antiproliferative factor (APF) isolated from the urine of patients with interstitial cystitis wherein the APF is characterized by a molecular weight of about 1.7 kDa determined by mass spectrometry on a sample in an aqueous acetonitrile solution and a pI range of about 1.38-3.5, and the APF is capable of inhibiting normal human bladder epithelial (HBE) and bladder carcinoma cell proliferation. Picomolar quantities of HPLC-purified APF were able to induce several changes in normal bladder epithelial cells in vitro, including significantly decreased rates of proliferation (Keay et al., 2003) and decreased production of a growth factor required for log-phase growth of bladder epithelial cells (heparin-binding epidermal growth factor-like growth factor, or HB-EGF) (Keay et al., 2000; Keay et al., 2003).

HB-EGF has been previously described (for example, see U.S. Pat. No. 5,811,393). U.S. Pat. No. 6,156,522 describes a method for diagnosing interstitial cystitis in a subject suffering from bladder dysfunction, said method comprising the steps of (a) measuring the levels of HB-EGF-like growth factor in the urine sample of the subject; and (b) comparing said level with normal levels, wherein decreased levels of heparin-binding epidermal growth factor-like growth factor, as compared to levels of heparin-binding epidermal growth factor-like growth factor in a normal population, indicates the presence of interstitial cystitis. U.S. Pat. No. 6,232,289 teaches a method for enhancing bladder epithelial cell proliferation in a subject in need thereof, said method comprising administering to the subject HB-EGF, in an amount effective to enhance bladder epithelial cell proliferation. U.S. Pat. No. 6,376,197 teaches a method for diagnosing a condition such as interstitial cystitis associated with inhibited bladder epithelial cell proliferation comprising the steps of determining the level of epidermal growth factor in urine from the subject; and comparing said level with normal level, according to the following criterion: increased level of epidermal growth factor, as compared to level of epidermal growth factor in a normal population, indicates the presence of the condition.

Microarray analysis indicated that APF can also induce changes in the pattern of cellular gene expression toward a more differentiated phenotype (Keay et al., 2003). Identification of this factor is therefore important for determining its potential role in the pathogenesis of interstitial cystitis and establishing its utility as a biomarker for this disease.

Preliminary characterization of APF indicated that it was a low molecular weight, relatively heat stable peptide (Keay et al., 2000). APF is found in minute quantities in both patient urine specimens and explanted patient bladder cell supernatants, making conventional methods of structural analysis, such as NMR spectroscopy, unfeasible. As described herein, the complete characterization of this potent growth inhibitor provides a novel structure not previously disclosed. The complete characterization was made using a combination of techniques including mass spectrometry, lectin affinity chromatography, enzymatic analysis, and total synthesis.

Confirmation of the structure of APF was provided using microcapillary liquid chromatography of native and synthetic APF derivatives, as well as by demonstration of synthetic APF's ability to regulate growth factor production and bladder epithelial cell proliferation. Additional evidence of APF's identity was provided by identification of mRNA that bound to a probe for the frizzled 8-protein segment in cells from interstitial cystitis patients but not controls, as well as by binding of rabbit antibodies raised against synthetic APF to purified native APF from supernatants of bladder epithelial cells of interstitial cystitis patients.

Another factor considered to be a cell cycling inhibitory factor is described in U.S. Pat. No. 5,916,871, wherein the factor comprises a sialylated glycopeptide preferably having a molecular weight much larger (e.g. 18 kD or 66 kD) than APF and that inhibits the G1 phase (but not G2) of the cell cycle. This previously described factor also had a carbohydrate component that accounted for less than 10% of its total mass, whereas APF in its native form has carbohydrate that accounts for 44% of its total mass.

Other and further objects, features, and advantages will be apparent from the following description of the presently preferred embodiments of the invention, which are given for the purpose of disclosure.

BRIEF SUMMARY OF THE INVENTION

The present invention is directed to a system and method that concern an antiproliferative factor (APF). In particular aspects of the invention, the APF is associated with, related to, localized in, or otherwise provided in vitro; in vivo in an organism, such as in a mammal, including a human; and/or ex vivo, as in a particular tissue, fluid, or organ. It is also contemplated that APF is provided by lower life forms, such as *Drosophila*, because it bears homology to a segment of a protein found in animals such as humans, mice, and *Drosophila*. The APF may be associated with a particular tissue, fluid, or organ from an organism. In specific embodiments, the APF is secreted by cells in the particular tissue, fluid, or organ, and in additional embodiments the APF is active in the particular tissue, fluid, or organ, such as being active in cells comprised therein. In some embodiments the APF is secreted by and active in cells of a particular tissue, fluid, or organ. In a particular aspect, the APF is associated with tissues comprising epithelial cells, including the following: urinary bladder; ureter; urethra; lung; heart; gastrointestinal tract (including the stomach, small intestine, large intestine, rectum, liver, pancreas and gall bladder); spleen; male reproductive tract, including the seminal vesicles, prostate, bulbourethral gland, vas deferens, epididymis, testes, and penis; female reproductive tract, including the ovaries, Fallopian tubes, uterus, cervix, and vagina; kidneys; adrenal glands; thymus; thyroid; skin; bone (including synovium); ocular tissues (including cornea, retina, and lens); cochlea; breast tissue; lymph nodes; oral mucosa (including gingival), salivary gland, parotid gland; and nasopharygeal mucosa (including sinus mucosa), for example.

In certain embodiments of the present invention, the inventive compound comprises an isolated APF molecule. The APF molecule of the present invention comprises a glycopeptide that inhibits in part or in full cell proliferation and/or slows cell proliferation, for example. In specific embodiments, the cell being proliferated is an epithelial cell. In particular embodiments, APF may be considered a negative growth factor, negative growth regulator, or toxin. Although in specific embodiments the APF is a urinary bladder-specific APF or a urinary bladder epithelial cell-specific APF, it is also useful for other tissues, such as to inhibit the proliferation of non-bladder cells, including fibroblasts or prostate cells, for example. Because interstitial cystitis patients have the same alterations in the serum levels of HB-EGF and EGF in serum as seen in urine specimens (Keay et al., 2000), APF in some embodiments is produced in tissues other the urinary bladder.

As delineated in Rashid et al. (2004), in specific embodiments APF is a cell-cycle modulator. That is, explanted cells from normal bladder biopsy specimens were exposed to APF, which increased significantly the proportion of tetraploid and hypertetraploid cells compared to controls. Thus, in a particular aspect of the invention, exposure of a cell to APF provides a block in cell cycling in the G2 and/or M phase cell cycle block and/or the production of polyploidy. As such, APF affects cell cycle distribution, which in particular embodiments contributes at least in part to the pathogenesis of bladder disorders such as interstitial cystitis, for example through disruption of normal urothelial proliferation and repair processes. In further embodiments, exposure of one or more cells to APF results in inhibition of proliferation of the one or more cells, which may comprise a cell cycle block at any point in the cell cycle, although in particular embodiments the block is primarily in G2 or M phase. In particular embodiments, removal of APF permits the cell cycle to resume.

In particular embodiments, the molecular weight of APF is less than about 3000 Daltons, although in alternative embodiment the molecular weight of APF is more than about 3000 Daltons. The composition may be further defined as comprising a sugar moiety and a hydrophobic moiety, wherein the hydrophobic moiety may be a peptide moiety or a lipid moiety. Particular peptide moieties include any suitable structure, although in specific embodiments they may be linear, cyclical, branched, or a combination thereof, for example. In further specific embodiments, the peptide moiety comprises homology to at least part of a frizzled polypeptide, such as having homology to at least part of a transmembrane domain of frizzled 8, such as one comprised in the exemplary sequence described in NP_114072 (SEQ ID NO:7), encoded by the exemplary polynucleotide in NM_031866 (SEQ ID NO:8). In other specific embodiments, the peptide component of APF comprises total or substantially total homology to at least part of the putative sixth transmembrane domain of frizzled 8, a G-protein coupled receptor whose natural ligand is Wnt, an important regulator of cell proliferation. An example of a secreted frizzled related protein is described in U.S. Pat. No. 6,600,018, which is incorporated by reference herein in its entirety.

For example, the peptide moiety may comprise less than about 50%, about 50% homology to at least part of frizzled 8, about 55% homology, about 60% homology, about 65% homology, about 70% homology, about 75% homology, about 80% homology, about 85% homology, about 90% homology, about 95% homology, or 100% homology. A skilled artisan is aware, however, that in those embodiments involving, for example, peptide mimetics sequence homology is not used to determine functionality, but rather chemical characteristics of hydrophobicity and physical and chemical similarities (i.e. polarity, steric bulk, hydrogen boding capabilities).

In an object of the invention, APF is a sensitive and specific biomarker for a bladder disorder such as interstitial cystitis (IC), and in a specific embodiment it plays a critical role in the pathogenesis of IC by profoundly inhibiting bladder cell proliferation, such as via regulation of gene expression (such as by increased E-cadherin production, for example) and alterations in the production of specific growth factors (such as HB-EGF and EGF, for example). More specifically, the inhibition of bladder cell proliferation by APF involves inhibition of HB-EGF production; stimulation of cellular EGF, E-cadherin, arylsulfatase A, phosphoribosylpyrophosphate synthetase-associated protein 39, or SWI/SNF complex 170 kDa subunit gene expression; or inhibition of cellular putative tRNA synthetase-like protein, vimentin, neutral amino acid transporter B, possible GTP-binding protein, alpha 1 catenin, alpha 2 integrin, cyclin D1 and JNK or ribosomal protein L27a gene expression.

In one specific aspect of the invention, APF is an acidic, heat stable sialoglycopeptide comprising 9 amino acid residues (such as, for example, TVPAAVVVA, SEQ ID NO:1; SVPAAVVVA, SEQ ID NO:3; TVPAAVVLA, SEQ ID NO:4; or SLPAAVVVA, SEQ ID NO:5) covalently linked through the N-terminal threonine, serine, or cysteine, for example, to an N-acetylgalactosamine or N-acetylglucosamine residue (wherein the glycosylated N-acetylgalactosamine sialoglycopeptide for these specific peptides is respectively SEQ ID NO: 11, SEQ ID NO:12, SEQ ID NO:13, or SEQ ID NO:14 and the glycosylated N-acetylglucosamine sialoglycopeptide for these specific peptides is respectively SEQ ID NO:15, SEQ ID NO:16, SEQ ID NO:17, or SEQ ID NO:18) that is linked via an α or β configuration to galactose, and sialylated on the galactose moiety via 2,3 linkage. The anomeric configuration of the glycosyl bond is alpha in particular embodiments, although it may be beta in alternative embodiments.

In a specific embodiment of the present invention, the peptide component of APF is hydrophobic and may be substituted for a non-proteinaceous moiety that is also hydrophobic, such as a lipid. Thus, in particular aspects of the invention, the peptide/lipid moiety of APF facilitates association with a membrane, such as being inserted, linked, bound, intercalated, or otherwise associated thereto, or, alternatively, by binding to a membrane surface receptor, and the sugar moiety of native APF comprises a high level of the functional activity of the molecule.

The present invention encompasses isolated naturally-existing APF, synthetic APF, derivatives thereof, or mixtures thereof. Like native APF, synthetic APF profoundly inhibited bladder epithelial cell proliferation ($IC_{50}$=0.4 nM) and HB-EGF production, while stimulating EGF production. Synthetic APF also inhibited proliferation of bladder carcinoma cells that are sensitive to native APF. In specific embodiments of the invention, desialylated native APF and nonsialylated synthetic APF comprise functional activity as their sialylated counterparts, although nonglycosylated synthetic peptide and the beta anomer of glycosylated synthetic APF comprised less desirable activity.

In one embodiment, the APF compound comprises a sugar moiety having one or more sugars, wherein the sugars are referred to herein as a first sugar, a second sugar, a third sugar, and so forth. Although any of the sugars may be covalently linked to a peptide, for example, in specific embodiments the third sugar is covalently linked to a peptide, such as one having a sequence essentially as set forth in SEQ ID NOS:1, 3, 4, or 5, or it may be alternatively linked to a lipid molecule. The sugar moiety may include naturally-occurring sugars, synthetic sugars, derivatives thereof including sugar mimetic components, and/or any combination thereof.

Certain compounds of the present invention comprise a peptide moiety, which may be characterized by having a terminal subunit having a polar chemical characteristic and/or a heteroatom therein. The subunits of the peptide may include naturally-occurring amino acid residues, unnatural amino acids, derivatives of amino acids, such as methylated amino acids, peptidomimetic components and/or any combination thereof. In alternative embodiments, the peptide moiety is replaced with a lipid molecule, such as an omega fatty acid, including myristic or palmitic acid, or other lipids such as phosphatidylcholine, phosphatidylethanolamine, and the like.

In preferred embodiments, the sugar molecule includes one or more of a sialic acid, galactose, glucose, N-acetylglucosamine, and/or N-acetylgalactosamine, for example. In certain embodiment, the sialic acid molecule is covalently linked to the galactose or glucose through a (2, 3), a (2, 6), a (2, 8), and/or a (2,9) linkage. A skilled artisan is aware of the nomenclature used in sugar/carbohydrate chemistry to identify the atom at the locations specified. Alternatively, the galactose or glucose is covalently linked to the N-acetylgalactosamine or N-acetylglucosamine molecule through a 1->3, a 1->6 or a 1->4 linkage. In a further preferred embodiment, the N-acetylgalactosamine or N-acetylglucosamine sugar molecule is linked to the hydrophobic moiety in the alpha configuration.

In those compositions of the present invention comprising a lipid moiety, the lipid moiety may be a saturated fatty acid such as, for example, caprylic acid, capric acid, lauric acid, myristic acid, palmitic acid, or stearic acid; an unsaturated fatty acid such as, for example, palmitoleic acid, oleic acid, linoleic acid, ricinoleic acid, and/or arachindonic acid; esterified fatty acids such as, for example, steroid alcohols in which an ester is added to an alcohol on the lipid; omega fatty acids, including myristic and palmitic acids; phosphate-containing fats such as, for example, phosphatidylcholine and phosphatidylethanolamine; or surfactants characterized by having a polar head and a non-polar tail. In general, the critical property of the lipid is the chemical characteristic of hydrophobicity such that the lipid is able to associate, intercalate or otherwise bind to a bilayer lipid cell membrane.

Also contemplated are derivatives of APF in which the peptide having a sequence essentially as set forth in SEQ ID NO:1 is a fragment thereof, wherein the fragment is 1 to about 8 amino acids of SEQ ID NO:1. Analogous fragments are contemplated for SEQ ID NO:3, SEQ ID NO:4, SEQ ID NO:5, and SEQ ID NO:6. It is further contemplated that the peptide moiety may be a nonapeptide or longer than a nonapeptide, such as having 10 or more amino acids in the peptide moiety, or having 15 or more amino acids in the peptide moiety.

It is contemplated that among the derivatives of APF are natural precursors or metabolites of APF. Further, natural or synthetic APF or their derivatives may be labeled with a detectable molecule such as, for example, a fluorescent, colorimetric, or radioactive moiety. In all cases, the compounds of the present invention alter cellular functions in a manner similar to or identical to the alterations affected by native APF. Examples of cellular functions altered by APF include inhibition of HB-EGF production; stimulation of cellular EGF, E-cadherin, arylsulfatase A, phosphoribosylpyrophosphate synthetase-associated protein 39, or SWI/SNF complex 170 kDa subunit gene expression; or inhibition of cellular putative tRNA synthetase-like protein, vimentin, neutral amino acid transporter B, possible GTP-binding protein, alpha 1 catenin, alpha 2 integrin, cyclin D1 and JNK or ribosomal protein L27a gene expression.

Oligonucleotides that encode the nonapeptide of SEQ ID NO:1 or biologically functional derivatives thereof, such as the peptides of SEQ ID NO:3, SEQ ID NO:4, or SEQ ID NO:5, for example, and/or precursors of APF are also contemplated herein. An exemplary oligonucleotide that encodes SEQ ID NO:1 is SEQ ID NO:2. However, given the limited choices of triplet nucleotides per given codon for a particular amino acid, a skilled artisan recognizes that a polynucleotide encoding a peptide of the invention, exemplary embodiments of which include SEQ ID NO:1, SEQ ID NO:3, SEQ ID NO:4, SEQ ID NO:5, or SEQ ID NO:6 are limited in number and are well within the scope of the invention. This is particularly true given the further subset of codons available for encoding hydrophobic amino acids, which are preferably comprised in at least part of the peptide moiety of the APF molecule.

Compositions comprising the APF compounds of the present invention are contemplated. The compositions may further comprise a delivery agent, such as a liposome; encapsulated cell; conjugated molecules, such as antibodies (Safavy et al., 2003), other peptides, and a variety of non-peptide conjugates (including folate and polyethylene glycol; Aronov et al., 2003); drugs, such as geldanamycin (Mandler et al., 2004) or insulin (Ou et al., 2003); liposomes (Heath and Martin, 1986); lactosaminated human albumin (Di Stefano et al., 2003); polyethylene glycol (PEG) (Aronov et al., 2003); nanoparticles, such as colloidal gold; or other molecules that bind to cell surface receptors to facilitate cellular interaction with or uptake of APF.

Use of such novel compositions is another object of the present invention. Specifically, the present invention is directed to a diagnostic kit for the detection of a bladder disorder, more specifically interstitial cystitis, comprising a compound of the present invention. In specific embodiments, a diagnostic kit of the present invention comprises one or more antibodies to an epitope on the peptide, sugar, or glycopeptide moiety of an APF molecule. The antibodies may be polyclonal, monoclonal, or the kit may comprise both polyclonal and monoclonal antibodies.

In some aspects of the invention, there is a method that detects a bladder disorder in an individual by assaying for an APF molecule. In specific embodiments, the bladder disorder is interstitial cystitis. The present invention provides the advantage of being able to assay for an APF molecule by non-invasive means, although in alternative embodiments invasive means may be used. A sample may be obtained from the individual and assayed directly or indirectly for the APF molecule. In specific embodiments, the sample comprises urine, plasma, or other bodily fluid specimen, such as whole blood, feces, saliva, nipple aspirate, mucus, or sweat. A urine sample may be obtained following voiding from the individual, and it may be obtained via a catheter.

Diagnostic methods may comprise detection of one or more sugar moieties of the APF molecule and/or they may comprise detection of the peptide or lipid moieties or a combination of peptide and/or lipid and/or sugar moieties of the APF molecule. In specific embodiments, assaying steps comprise introduction to a sample an antibody directed to an epitope of the peptide moiety of an APF molecule. In embodiments wherein APF comprises a lipid moiety, this may be used for diagnosing utilizing suitable assaying means such as standard methods available to detect a lipid molecule.

The present invention is also directed to methods of treating epithelial hyperplasia or malignancies of epithelial origin comprising administering an effective amount of APF or derivatives thereof to a patient in need of such treatment.

The present invention is directed to methods of treating fibroblast hyperplasia or malignancy comprising administering an effective amount of APF or derivatives thereof to a patient in need of such treatment.

The present invention is directed to methods of treating lymphoreticular malignancies or solid tumors comprising administering an effective amount of APF or derivatives thereof to a patient in need of such treatment.

The present invention is directed to methods of treating cancer comprising administering an effective amount of APF or derivatives thereof to a patient in need of such treatment. Any kind of cancer may be treated, such as bladder, lung, breast, prostate, brain, stomach, colon, spleen, liver, pancreatic, melanoma, head and neck, thyroid, and so forth. In specific embodiments, though, the invention is useful for treating bladder or prostate cancer, comprising co-administering an effective amount of APF or derivatives thereof to a patient in need of such treatment. In additional aspects of the invention, the APF improves, facilitates, or assists in overcoming resistance or improving sensitivity to a cancer therapy selected from the group of chemotherapy, radiotherapy, surgery gene therapy, and/or immunotherapy.

The compounds of the present invention also have antiangiogenic properties and are contemplated for use in methods of treatments benefiting from inhibiting or slowing the formation and/or differentiation of blood vessels, such as blood vessels that feed a tumor.

The APF compounds of the present invention are also useful as an antifungal agent.

The APF compounds may be used to generate antibodies thereto, in which the antibodies may be used for treating interstitial cystitis. In particular embodiments, the present invention encompasses generating antibodies against a peptide moiety, sugar moiety, and/or glycopeptide moiety of an APF composition. For example, antibodies are generated against a peptide moiety of APF, such as one comprising SEQ ID NO:1, SEQ ID NO:3, SEQ ID NO:4, SEQ ID NO:5, or SEQ ID NO:6, for example. The antibodies that are generated may be polyclonal or monoclonal. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" may also be used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference). Antibodies of the invention are prepared by immunizing an animal with a composition in accordance with the present invention and collecting antisera from that immunized animal.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, or toxins, for example. Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

Alternatively, the APF compounds are used to prepare antisense oligonucleotides, small interfering RNA molecules, or other substances that inhibit APF production or activity.

In yet another embodiment, the APF compounds are used to generate an animal model for interstitial cystitis. In an exemplary animal model, the animal is stimulated to develop symptoms (such as bladder or pelvic pain, increased urinary frequency, and/or increased urinary urgency) or findings (such as thinning and/or ulceration of the bladder epithelium) associated with interstitial cystitis following exposure of the bladder epithelium to APF. This exposure could result from the direct administration of synthetic or native APF intravesically, or the expression/biosynthesis of APF by bladder epithelial cells following transfection with a polynucleotide encoding the peptide moiety of the APF molecule, for example. The gene can further be introduced into the cells by direct methods (such as electroporation or membrane fusion) or by indirect methods (such as via a viral vector). It should be noted that the sequence of mouse and human frizzled 8 is identical over the 9 amino acids that are homologous to the peptide moiety of the APF molecule, and mouse fibroblasts are sensitive to the antiproliferative effects of APF, allowing for the development of a mouse model for this disorder based on the APF. An exemplary human frizzled 8 polypeptide is SEQ ID NO:7, and an exemplary mouse frizzled 8 polypeptide is SEQ ID NO:9 (NP_032084).

In another embodiment, an APF composition is utilized in an animal model for psoriasis, such as one comprising spontaneous psoriasiform skin lesions (Schon, 1999). Other exemplary disease models include animal models for testing the effects of APF on hyperplasia, including a model comprising athymic, asplenic nude rats (Polo et al., 1999) and a hairless guinea pig model for keloid formation (Clugston et al., 1995).

In yet another embodiment, a method of detecting APF activity using a cell proliferation inhibition assay (such as inhibition of tritiated thymidine or bromodeoxyuridine incorporation, for example) using normal bladder epithelial cells or cells derived from bladder carcinomas is provided, wherein the presence of APF indicates interstitial cystitis is present or has the predisposition to develop. These methods are particularly advantageous, because they may be non-invasive, i.e., the sample may be a urine sample that may or may not be obtained via catherization. A urine sample may be obtained upon voiding from an individual.

In another embodiment, there is a method of detecting APF by completing a direct assay for the APF glycopeptide using an antibody-based method (such as ELISA), mass spectrometry (MS) or nuclear magnetic resonance (NMR), or a combination thereof.

The present invention also encompasses APF compositions for use as a stimulus, given the ability to stimulate specific cell signaling pathway(s), including (but not limited to) the Wnt signaling pathways.

In an embodiment of the present invention, there is an isolated or synthesized composition comprising a urinary bladder antiproliferative factor having one or more sugar moieties, wherein at least one sugar moiety is linked to a hydrophobic moiety. The composition may be further defined as a urinary bladder epithelial cell antiproliferative factor. The molecular weight of the factor may be less than about 3000 Daltons. In specific embodiments, the hydrophobic moiety comprises one of the following: a peptide moiety, which may be linear, cyclical, or branched; or a lipid moiety. The APF composition comprises a sialoglycopeptide, in specific embodiments, although in alternative embodiments it comprises a glycopeptide or a peptide. In additional embodiments, the peptide has homology to at least part of a frizzled polypeptide, such as having homology to at least part of a transmembrane domain of frizzled 8.

In particular embodiments, the composition is further defined as comprising about one to about six sugar moieties; and a peptide moiety of about two to about fifteen amino acid residues, wherein one of the residues is a linking amino acid, and wherein the peptide is linked to at least one of the sugar moieties at a heteroatom of the linking amino acid, which may be polar, such as a serine, a threonine, a cysteine, a lysine, an arginine, or a tyrosine. Thus, it is contemplated that the heteroatom linked to the sugar moiety is an oxygen, nitrogen and/or a sulfur atom. In further specific embodiments, the composition comprises three sugar residues and nine amino acids, wherein the linking amino acid is a serine or a threonine. In yet other specific embodiments, the composition comprises two sugar residues and nine amino acids The sugar moiety comprises a naturally occurring sugar, a synthetic sugar, a derivative of a naturally occurring sugar, or a derivative of a synthetic sugar. More specifically, at least one sugar moiety is an amino sugar such as a sialic acid (N-acetylneuraminic acid) molecule, and in some embodiments, and in some embodiments, the amino sugar is linked to at least another (second) sugar via a (2,3) linkage, a (2,6) linkage, a (2,8) linkage, or a (2,9) linkage. The linkage between at least one sugar moiety and a peptide moiety is a covalent linkage; the linkage between a sugar moiety and a lipid moiety is a covalent linkage; and other linkages described herein may be covalent.

In specific embodiments involving more than one sugar moiety, the linkage between one sugar moiety and another sugar moiety is a 1→3 linkage, a 1→4 linkage, or a 1→6 linkage. In other embodiments, the linkage between at least one sugar moiety and a hydrophobic moiety, such as a peptide or a lipid, is in the alpha or beta configuration.

The peptide moiety of the composition is further defined as comprising a naturally occurring amino acid, an unnatural amino acid, a derivative of a naturally occurring amino acid, a derivative of an unnatural amino acid, a modified amino acid, a backbone-modifying amino acid, or a mixture thereof. The peptide moiety is further defined as comprising one or more backbone-modifying amino acids that comprise reduced peptide bonds. Modified amino acids may be further defined as a methylated amino acid, an acetylated amino acid, a beta amino acid, or an amino acid mimetic.

The peptide moiety is about nine amino acids in length, in some aspects of the invention, and may comprise SEQ ID NO:1, SEQ ID NO:3, SEQ ID NO:4, or SEQ ID NO:5. The lipid moiety in specific embodiments comprises a saturated fatty acid such as, for example, caprylic acid, capric acid, lauric acid, myristic acid, palmitic acid, or stearic acid; an unsaturated fatty acid such as, for example, palmitoleic acid, oleic acid, linoleic acid, ricinoleic acid, arachindonic acid; esterified fatty acids such as, for example, steroid alcohols in which an ester is added to an alcohol on the lipid; omega fatty acids, including myristic and palmitic acids; or phophate-containing fats such as, for example, phosphatidylcholine and phosphatidylethanolamine; or surfactants characterized by having a polar head and a non-polar tail.

An APF composition of the present invention may be further defined as comprising a label, such as a fluorescent moiety, a colorimetric moiety, or a radioactive moiety. In certain embodiments, the label is attached to at least one of the one or more sugar moieties, such as sialic acid, glucose, galactose, N-acetylgalactosamine or N-acetylglucosamine. Alternatively, the label is attached any suitable atom in a peptide, such as within at least one of the amino acids making up the peptide moiety, such as at a heteroatom in a serine, threonine, or cysteine amino acid subunit, or attached to the carboxyl group at the carboxyl end of the peptide. Alternatively, the label is attached to at least one of the atoms of the lipid moiety such as at a double bond in an unsaturated fatty acid (i.e., oleic acid and the like), or at a polar head group of a lipid (alcohol).

In specific embodiments of the present invention, the APF composition is further defined as:
(a) Sialic acid-galactose-Nacetylgalactosamine-threonine-valine-proline-alanine-alanine-valine-valine-valine-alanine;
(b) Sialic acid-galactose-Nacetylglucosamine-threonine-valine-proline-alanine-alanine-valine-valine-valine-alanine; or (c) Sialic acid-galactose-Nacetylglucosamine-serine-leucine-proline-alanine-alanine-valine-valine-valine-alanine.

As described further in the Examples herein, the APF compositions of the present invention are alternatively defined as any one of (a), (b) or (c) without a sialic acid molecule.

The composition of (a) may be further defined as having one (or one or more) of the following: the sialic acid is linked to galactose via a 2,3 linkage; the galactose is linked to the N-acetylgalactosamine via a 1,3 linkage; and/or the N-acetylgalactosamine is linked to threonine via an O linkage in an alpha configuration.

The composition of (b) may be further defined as having one (or one or more) of the following: the sialic acid is linked to galactose via a 2,3 linkage; the galactose is linked to the N-acetylglucosamine via a 1,4 linkage; and/or the N-acetylglucosamine is linked to threonine via an 0 linkage in an alpha configuration.

The composition of (c) may be further defined as having one (or one or more) of the following: the sialic acid is linked to galactose via a 2,3 linkage; the galactose is linked to the N-acetylglucosamine via a 1,4 linkage; and/or the N-acetylglucosamine is linked to serine via an 0 linkage in an alpha configuration.

In some embodiments of the present invention, the composition further comprises a delivery vehicle, such as a liposome, a cell, a conjugated molecule, a nanoparticle, or a mixture thereof. The conjugated molecule may comprise an antibody, a peptide, folate, polyethylene glycol, a drug, a liposome, a microsphere, or lactosaminated human albumin. The nanoparticle may comprise colloidal gold.

The composition may be comprised in a pharmaceutically acceptable excipient. The composition may also reversibly arrest cell proliferation. In specific embodiments, the composition is further defined as comprising activity for arresting cell cycling primarily in G2 or M phase or both.

In other embodiments of the present invention, there is an isolated peptide selected from the group consisting of SEQ ID NO:1; SEQ ID NO:3; SEQ ID NO:4; SEQ ID NO:5, or a functional derivative thereof. The functional derivative thereof may be further defined as comprising a conservative substitution at one or more amino acids of the peptide. The conservative substitution may be further defined as a substitution at serine, threonine, proline, or a combination thereof. In specific embodiments, the conservative substitution comprises a hydrophobic conservative substitution, such as a substitution at one or more alanines, one or more valines, one or more prolines; or a combination thereof. In specific embodiments, a function of peptides of the invention contemplated here is for use as a standard in a kit (such as to quantify APF in samples; as an antiproliferative factor; and/or as a means for inducing antibody production.

In additional embodiments of the present invention, there is an isolated polynucleotide encoding SEQ ID NO:1, which may be further defined as SEQ ID NO:2.

The polynucleotides may be further defined as having one or more of the following: a codon for threonine selected from the group consisting of ACA, ACC, ACG, and ACU; a codon for one or more valines selected from the group consisting of GUA, GUC, GUG, and GUU; a codon for proline selected from the group consisting of CCA, CCC, CCG, and CCU; and a codon for one or more alanines selected from the group consisting of GCA, GCC, GCG, and GCU.

In another embodiment, there is an isolated polynucleotide encoding SEQ ID NO:3, such as one further defined as having one or more of the following: a codon for serine selected from the group consisting of AGC, AGU, UCA, UCC, UCG, and UCU; a codon for one or more valines selected from the group consisting of GUA, GUC, GUG, or GUU; a codon for proline selected from the group consisting of CCA, CCC, CCG, or CCU; and a codon for one or more alanines selected from the group consisting of GCA, GCC, GCG, or GCU.

In an additional embodiment, there is an isolated polynucleotide encoding SEQ ID NO:4, such as one further defined as having one or more of the following: a codon for threonine selected from the group consisting of ACA, ACC, ACG, and ACU; a codon for one or more valines selected from the group consisting of GUA, GUC, GUG, and GUU; a codon for proline selected from the group consisting of CCA, CCC, CCG, and CCU; a codon for one or more alanines selected from the group consisting of GCA, GCC, GCG, and GCU; and a codon for leucine selected from the group consisting of UUA, UUG, CUA, CUC, CUG, and CUU.

In another embodiment of the present invention, there is an isolated polynucleotide encoding SEQ ID NO:5, such as one further defined as having one or more of the following: a codon for serine selected from the group consisting of AGC, AGU, UCA, UCC, UCG, and UCU; a codon for leucine selected from the group consisting of UUA, UUG, CUA, CUC, CUG, and CUU; a codon for proline selected from the group consisting of CCA, CCC, CCG, and CCU; a codon for one or more alanines selected from the group consisting of GCA, GCC, GCG, and GCU; and a codon for one or more valines selected from the group consisting of GUA, GUC, GUG, and GUU.

In additional embodiments of the present invention, there is a kit, comprising the APF composition housed in a suitable container. There may be a kit for use in diagnosing a bladder disorder in a subject, comprising an antibody composition that binds immunologically to an epitope of a peptide, sugar, or glycopeptide epitope of an antiproliferative factor, said antibody composition housed in a suitable container. In specific embodiments, the antiproliferative factor is a urinary bladder antiproliferative factor. The peptide may comprise one or more hydrophobic amino acids.

In a specific embodiment, the antibody binds immunologically to an epitope of SEQ ID NO:1 or a glycopeptide derivative thereof (SEQ ID NO:19) and/or the peptide comprises an epitope of SEQ ID NO:1 and is about 2 to 15 amino acids in length; the antibody binds immunologically to an epitope of SEQ ID NO:3 or a glycopeptide derivative thereof (SEQ ID NO:20) and/or the peptide comprises an epitope of SEQ ID NO:3 and is about 2 to 15 amino acids in length; the antibody binds immunologically to an epitope of SEQ ID NO:4 or a glycopeptide derivative thereof (SEQ ID NO:21) and/or the peptide comprises an epitope of SEQ ID NO:4 and is about 2 to 15 amino acids in length; the antibody binds immunologically to an epitope of SEQ ID NO:5 or a glycopeptide derivative thereof (SEQ ID NO:22) and/or the peptide comprises an epitope of SEQ ID NO:5 and is about 2 to 15 amino acids in length; and/or the antibody binds immunologically to an epitope of SEQ ID NO:6 or a glycopeptide derivative thereof (SEQ ID NO:23) and/or the peptide comprises an epitope of SEQ ID NO:6 and is about 2 to 15 amino acids in length.

Antibodies in the kit may include monoclonal antibodies; polyclonal antibodies, or both. The antibody may be labeled.

A kit of the present invention comprises a detection means for detecting APF compositions in a sample and includes antibodies, markers such as fluorescent reporter molecules, and/or capture molecules that target a sugar or peptide moiety of the composition, in additional embodiments.

In another embodiment of the present invention, there is a composition comprising antibodies or binding portions thereof, wherein said antibodies or binding portions bind to a peptide, sugar, or glycopeptide moiety of a urinary bladder antiproliferative factor, wherein said antiproliferative factor comprises one or more sugar moieties. In specific embodiments, the antibodies or binding portions bind to a peptide moiety of the antiproliferative factor and inhibit activity of the APF molecule thereby. The antibodies may be polyclonal antibodies, monoclonal antibodies, or a mixture thereof. In specific embodiments, the peptide is SEQ ID NO:1, SEQ ID NO:3, SEQ ID NO:4, or SEQ ID NO:5.

In an additional embodiment of the present invention, there is a method of detecting a bladder disorder in an individual, comprising the step of assaying for an APF composition. In specific embodiments, the bladder disorder is interstitial cystitis. In specific embodiments, the assaying step is non-invasive or invasive to the individual. In specific embodiments, the method is further defined as obtaining a sample from the individual; and assaying said sample for the presence of the APF composition. The sample may comprise urine, plasma, serum, tissue, or a mixture thereof from the individual. The assaying step may comprise detection of one or more sugar moieties of an APF composition. The assaying step may comprise detection of the hydrophobic moiety of the APF composition. The hydrophobic moiety of the composition may comprise a peptide moiety and the assaying step is further defined as comprising introduction to the sample of an antibody directed to an epitope of a peptide, sugar, or glycopeptide moiety of an APF composition. In specific embodiments, the assaying method comprises ELISA, Western blot, immunoblot, radioimmunoassay, immunohistochemistry, or other antibody-based detection methods, including slot blots, dot blots and so forth. In other embodiments, the assaying method comprises in situ hybridization or other means for detecting messenger mRNA for APF, for example. In still further embodiments, the assaying method comprises mass spectrometry, nuclear magnetic resonance, or other non-immunological methods for detecting peptide species.

In an additional embodiment of the present invention, there is a method of treating cancer, comprising the step of administering a therapeutically effective amount of an APF composition. In specific embodiments, the cancer comprises an epithelial cancer, such as bladder cancer or prostate cancer. In an additional specific embodiment, the method further comprises an additional cancer therapy, such as surgery, chemotherapy, radiation, gene therapy, immunotherapy, or a combination thereof.

In another embodiment of the present invention, there is a method of treating a bladder disorder, comprising the step of administering a therapeutically effective amount of an APF composition. In a specific embodiment, the method further comprises an additional bladder disorder therapy. In a specific embodiment, the bladder disorder comprises bladder cancer. In an additional specific embodiment, the method further comprises an additional cancer therapy, such as surgery, chemotherapy, radiation, gene therapy, immunotherapy, or a combination thereof.

In an additional embodiment, there is a method of treating a hyperplasia, comprising the step of administering a therapeutically effective amount of an APF composition. In a specific embodiment, the method further comprises an additional therapy for the hyperplasia, such as an epithelial hyperplasia or a fibroblast hyperplasia.

In another embodiment, there is a method of enhancing cancer treatment of an individual, comprising administering to the individual a therapeutically effective amount of an APF composition. Administration of the composition may enhance chemotherapy, radiotherapy, immunotherapy, gene therapy, or a combination thereof. The composition may be administered prior to the cancer treatment being enhanced, concomitant with the cancer treatment being enhanced, subsequent to the cancer treatment being enhanced, or a combination thereof.

In an additional embodiment, there is a method of inhibiting angiogenesis in an individual, comprising administering to the individual a therapeutically effective amount of an APF composition.

In another embodiment, there is a method of inhibiting fungal growth in an individual, comprising administering to the individual a therapeutically effective amount of an APF composition.

In one embodiment of the invention, there is an isolated or synthesized composition comprising a urinary bladder antiproliferative factor having one to six sugar moieties, wherein at least one sugar moiety is linked to a peptide moiety of about two to fifteen amino acid residues, wherein said peptide moiety comprises D-proline. In a specific embodiment, the peptide comprises one or more of an amino acid selected from the group consisting of threonine, valine, alanine, serine, and leucine. In some embodiments, one of the residues of the peptide is a linking amino acid, and wherein the linking amino acid comprises a heteroatom covalently linked to one of the sugar moieties. The linking amino acid may be a serine, threonine, or cysteine. The composition may be further defined as comprising two sugar residues and nine amino acids, wherein said linking amino acid is a serine, a threonine or a cysteine. In specific embodiments, the linkage between the sugar and the peptide is in the alpha or beta configuration. In particular cases, the linkage between the sugar and the peptide is in alpha configuration. In particular embodiments, the peptide moiety comprises SEQ ID NO:1, SEQ ID NO:3, SEQ ID NO:4, SEQ ID NO:5, SEQ ID NO:6, or functional derivatives thereof. The functional derivative of the peptide moiety comprising SEQ ID NO:1, SEQ ID NO:3, SEQ ID NO:4, SEQ ID NO:5, or SEQ ID NO:6 may comprise a conservative substitution at one or more amino acids of the peptide. The conservative substitution may be further defined as a substitution at a serine, threonine, or a combination thereof. In specific embodiments, the conservative substitution comprises a hydrophobic conservative substitution, such as a substitution at one or more alanines, one or more valines, one or more prolines; or a combination thereof.

In specific embodiments, there is a composition comprising (a) Sialic acid-galactose-Nacetylgalactosamine-threonine-valine-proline-alanine-alanine-valine-valine-valine-alanine; (b) Sialic acid-galactose-Nacetylglucosamine-threonine-valine-proline-alanine-alanine-valine-valine-valine-alanine; or (c) Sialic acid-galactose-Nacetylglucosamine-serine-leucine-proline-alanine-alanine-valine-valine-valine-alanine. In specific embodiments, the composition is further defined as having one or more of the following: the sialic acid is linked to galactose via a 2,3 linkage; the galactose is linked to the N-acetylgalactosamine via a 1,3 linkage; or the N-acetyl galactosamine is linked to threonine via an O linkage in an alpha configuration. In some embodiments, the composition of (b) is further defined as having one or more of the following: the sialic acid is linked to galactose via a 2,3 linkage; the galactose is linked to the N-acetylglucosamine via a 1,4 linkage; or the N-acetyl glucosamine is linked to threonine via an O linkage in an alpha configuration. In certain embodiments, the composition is further defined as having one or more of the following: the sialic acid is linked to galactose via a 2,3 linkage; the galactose is linked to the N-acetylglucosamine via a 1,4 linkage; or the N-acetylglucosamine is linked to serine via an O linkage in an alpha configuration. Compositions of the present disclosure may comprise a delivery vehicle, such as a liposome, a cell, a conjugated molecule, a nanoparticle, or a mixture thereof. The conjugated molecule may comprise an antibody, a peptide, folate, polyethylene glycol, a drug, a liposome, or lactosaminated human albumin. In specific embodiments, the nanoparticle comprises colloidal gold. The composition may be comprised in a pharmaceutically acceptable excipient. In specific embodiments of the composition, the amino acid that is third from the N-terminus of the peptide is proline.

In one embodiment, there is an isolated or synthesized composition comprising a urinary bladder antiproliferative factor, wherein the composition comprises two sugars and a peptide that comprises SEQ ID NO:1 (TVPAAVVVA), wherein the proline is a D amino acid, and wherein the sugars are β-galactose and N-acetyl galactosamine, wherein the N-acetyl galactosamine is linked to the peptide in the alpha configuration.

In one embodiment, there is a kit, comprising an isolated or synthesized composition comprising a urinary bladder antiproliferative factor having one to six sugar moieties, wherein at least one sugar moiety is linked to a peptide moiety of about two to about fifteen amino acid residues, wherein said peptide moiety comprises D-proline, and wherein the composition is housed in a suitable container.

In a particular embodiment, there is a method of treating a bladder disorder in an individual, comprising the step of administering to the individual a therapeutically effective amount of an isolated or synthesized composition comprising a urinary bladder antiproliferative factor having one to six sugar moieties, wherein at least one sugar moiety is linked to a peptide moiety of about two to about fifteen amino acid residues, wherein said peptide moiety comprises D-proline. In a specific embodiment, the bladder disorder is interstitial cystitis. The method may further comprise an additional interstitial cystitis treatment. The bladder condition may comprise interstitial cystitis, chronic pelvic pain syndrome, irritable bladder syndrome, urethral syndrome, painful bladder syndrome, or chronic nonbacterial prostatitis. In a specific embodiment, the individual has one or more symptoms selected from the group consisting of abdominal pain, urethral pain, vaginal pain, pain with sexual intercourse, urgency, bladder pressure, bladder spasms, increased day frequency of urination, and increased night frequency of urination.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.:

In FIG. 1A, there is molecular mass analysis of the active peak from microcapillary fractionation of HPLC-purified APF. FIGS. 1B and 1C provide analysis following successive fragmentation of predominant species by collision-induced dissociation.

DETAILED DESCRIPTION OF THE INVENTION

I. Definitions

Figure 1:
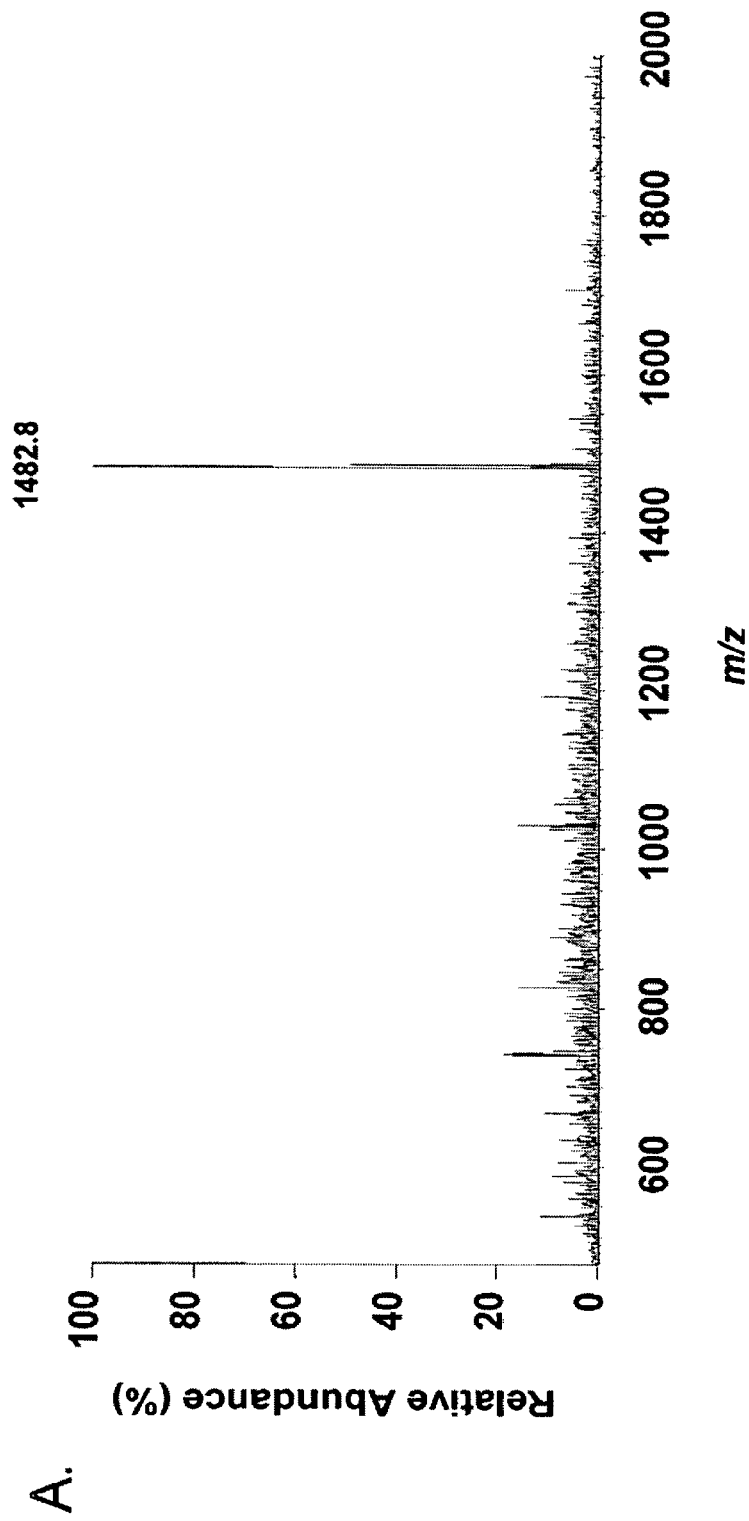
FIGS. 1A-1C show ion trap mass spectrometric analysis of APF.
Figure 1:
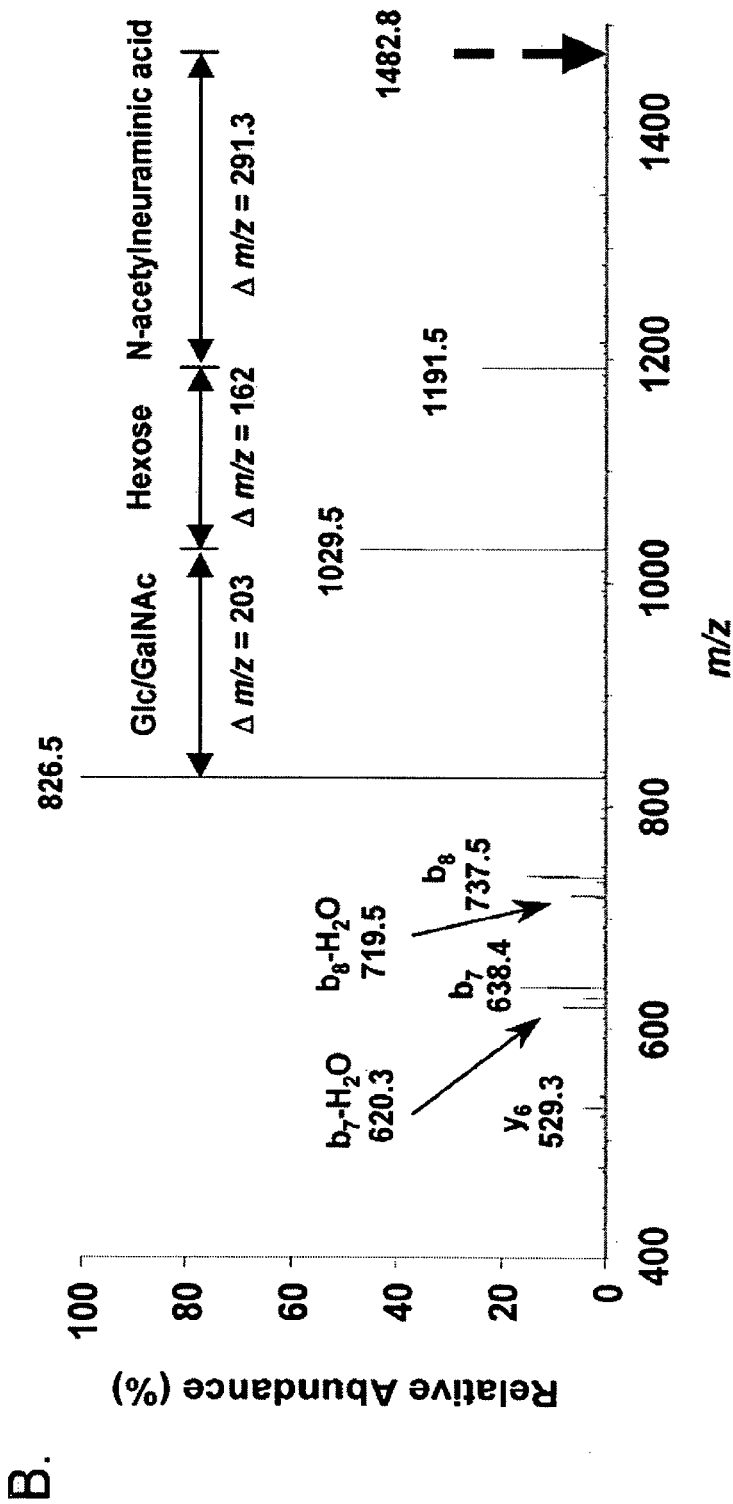
Figure 1:
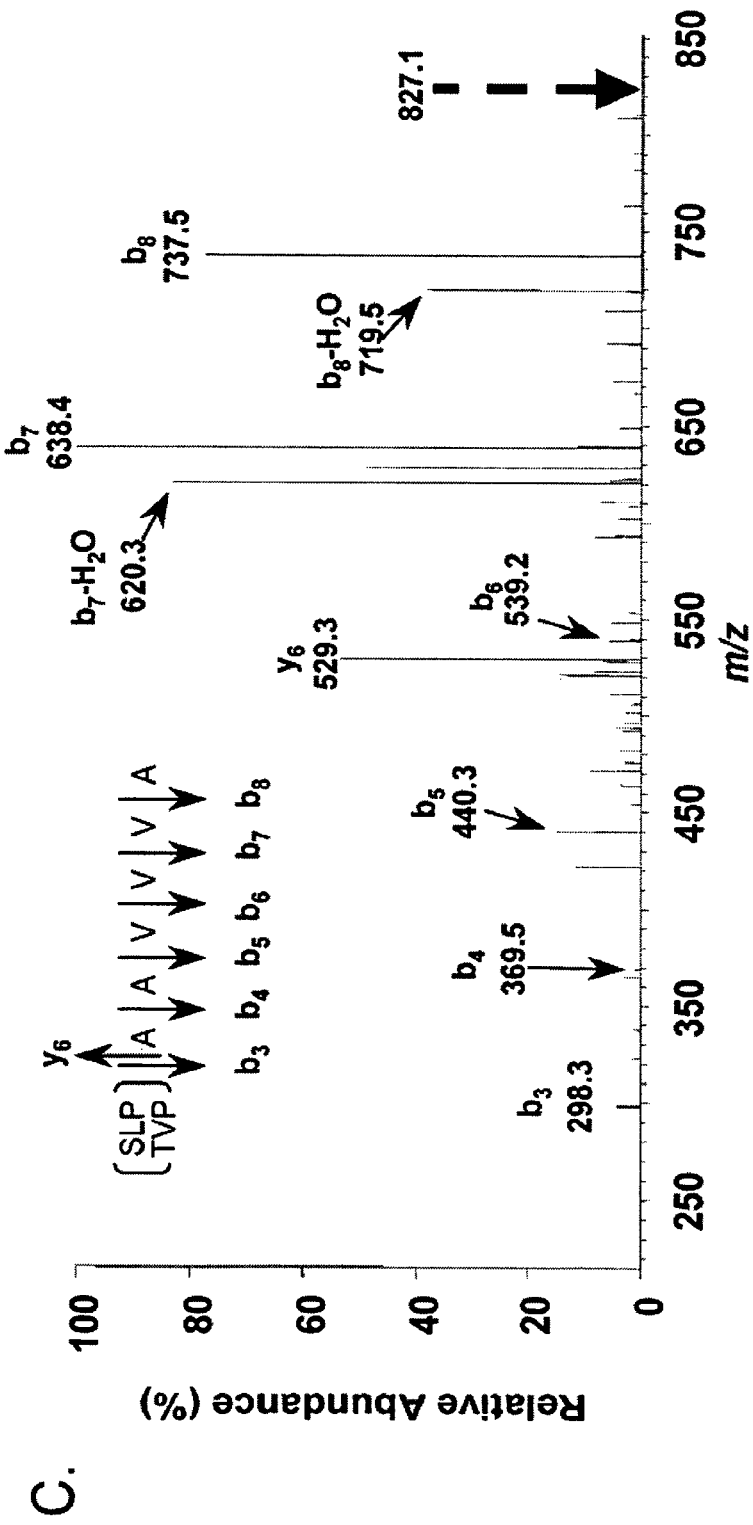

As used herein the specification, "a" or "an" may mean one or more. As used herein in the claim(s), when used in conjunction with the word "comprising", the words "a" or "an" may mean one or more than one. As used herein "another" may mean at least a second or more.

The term "alpha configuration" α as used herein refers to structural relationships in carbohydrate chemistry, wherein the anomeric group is in the axial configuration when the conformational formulation of the pyranose ring is used. Conversely, the term "beta configuration" α refers to that arrangement in which the anomeric group is equatorial.

The term "antiproliferative factor" as used herein refers to a molecule comprised of one or more sugar moieties and/or a hydrophobic moiety, wherein the molecule is characterized by the ability to inhibit cell proliferation. In specific embodiments, the inhibiting activity comprises inhibiting epithelial cell proliferation, such as bladder epithelial cell proliferation. In further specific embodiments, the hydrophobic moiety is a peptide or a lipid. In specific embodiments, the hydrophobic nature facilitates nonspecific association with a membrane, or specific or nonspecific interaction with a hydrophobic pocket of a membrane or cytoplasmic receptor, for example. In specific embodiments, the association with a membrane comprises insertion into a membrane. The membrane may be any kind of membrane, although in particular aspects of the invention it is a plasma membrane. In further specific embodiments, the peptide is hydrophobic in part and comprises enough hydrophobicity to facilitate association of APF with a membrane.

The term "backbone-modifying amino acid" is known in the art and is discussed as follows. Normal peptide or protein backbone is formed from polymerization of alpha amino acids, which have the amino group on the carbon adjacent to the carboxyl group. This produces a polymer in which the repeating unit is —[NHCH(R)C(O)]—, wherein R is the sidechain that makes each amino acid different, but the repeating unit that forms the back bone is as shown. If the amino group is moved to a different carbon, for example the beta-carbon of alanine, the backbone is no longer natural but still has many of the properties of peptides. Proteolytic enzymes do not recognize altered backbones. Beta-alanine or gamma-butyric acid are common backbone altering amino acids. They are not naturally found in peptides or proteins.

The term "bladder disorder" as used herein refers to an abnormal condition of the urinary bladder.

The term "conservative substitution" as used herein refers to replacing an amino acid in a peptide or polypeptide with a different amino acid of a similar chemical nature. For example, a nonpolar amino acid may be conservatively substituted with another nonpolar amino acid. In specific embodiments, a hydrophobic amino acid may be substituted with another hydrophobic amino acid.

The term "epithelial cancer" as used herein refers to a cancer in a tissue originating from epithelial cells of the tissue. For example, epithelial cancer may comprise urinary bladder; ureter; lung; heart; gastrointestinal tract (including the stomach, small intestine, large intestine, rectum, liver, pancreas and gall bladder); spleen; male reproductive tract, including the seminal vesicles, prostate, bulbourethral gland, vas deferens, epididymis, testes, and penis; female reproductive tract, including the ovaries, Fallopian tubes, uterus, cervix, and vagina; kidneys; adrenal glands; thymus; thyroid; skin; bone (including synovium); ocular tissues (including cornea, retina, and lens); cochlea; breast tissue; lymph nodes; oral mucosa (including gingival), salivary gland, parotid gland; and nasopharygeal mucosa (including sinus mucosa), for example.

The term "heteroatom" as used herein refers to an atom in an organic molecule that is other than carbon or hydrogen.

The term "hydrophobic" as used herein refers to lacking affinity for water.

The term "hydrophobic amino acid" as used herein refers to amino acids that are unable to form hydrogen bonds with water because they have no, or very small, electrical charges in their structure. In aqueous solution, hydrophobic amino acids disrupt the hydrogen bonding structure that is formed among water molecules, given that they are unable to contribute to it. Hydrophobic amino acids vary in size, and the majority of hydrophobic amino acids have a side chain that is purely hydrocarbon. Other things being equal, a larger hydrophobic side chain will be more strongly hydrophobic than a smaller one. Specific examples of hydrophobic amino acids include those that comprise aliphatic hydrocarbon side chains, such as alanine, valine, leucine, or isoleucine; aromatic side chains, such as phenylalanine or tryptophan; sulfur-comprising side chains, such as methionine; and/or imino acids, such as proline, for example. In particular embodiments, hydrophobic amino acids are considered to be alanine, valine, leucine, and isoleucine.

The term "hyperplasia" as used herein refers to the abnormal proliferation of normal cells in normal arrangement in a tissue.

The term "inhibitor of an antiproliferative factor" as used herein refers to an inhibitor of any APF as encompassed by the invention. In specific embodiments, the inhibitor degrades APF, blocks its effect on cell proliferation, that it is a growth factor, or a combination thereof, for example. In further specific embodiments, the inhibitor comprises an antibody, small interfering RNA, oligonucleotide, small molecule, and so forth, for example.

The term "peptide" as used herein refers to a compound made up of a single chain of D- or L-amino acids or a mixture of D- and L-amino acids joined by peptide bonds. Generally, the peptides used herein contain at least two amino acid residues and are less than about 50 amino acids in length. D-amino acids are represented herein by a lower-case one-letter amino acid symbol (e.g., r for D-arginine), whereas L-amino acids are represented by an upper case one-letter amino acid symbol (e.g., R for L-arginine). The peptides may be cyclical, linear, branched, or a combination thereof.

"Polypeptide" as used herein refers to a polymer of at least two amino acid residues and which contains one or more peptide bonds. "Polypeptide" encompasses peptides and proteins, regardless of whether the polypeptide has a well-defined conformation.

The term "protein" as used herein refers to a compound that is composed of amino acids linked by peptide bonds, but in contrast to peptides, has a well-defined conformation, such as a well-defined three-dimensional conformation. Proteins, as opposed to peptides, generally consist of chains of 50 or more amino acids.

The term "purified" as used herein, is intended to refer to a glycoprotein composition, wherein the glycoprotein is purified to any degree relative to its naturally-obtainable state, i.e., in this case, relative to its purity within a eukaryotic cell or within a fluid such as cell medium or supernatant, or a biological fluid such as urine, serum, or plasma.

A "subunit," as used herein, is a monomeric unit that is joined to form a larger polymeric compound. The set of amino acids are an example of subunits. Each amino acid shares a common backbone (—C—C—N—), and the different amino acids differ in their sidechains. The backbone is repeated in a polypeptide. A subunit represents the shortest repeating pattern of elements in a polymer backbone. For example, two amino acids of a peptide are not considered one subunit because two amino acids would not have the shortest repeating pattern of elements in the polymer backbone.

The term "terminal amino acid" as used herein refers to the amino acid on the end of a linear peptide of an APF molecule, and may refer to a N-terminal amino acid or a C-terminal amino acid.

The terms "therapeutic agent", "therapeutic composition", and "therapeutic substance" refer, without limitation, to any composition that can be used to the benefit of an organism including but not limited to a mammalian organism. Such agents may take the form of ions, small organic molecules, peptides, proteins or polypeptides, glycopeptides (and other modified peptides), oligonucleotides, and oligosaccharides, for example.

The term "therapeutically effective amount" as used herein refers to the amount of a composition utilized alone or in combination with another compound for a therapeutic purpose that results in ameliorating at least one symptom or objective finding (sign) of the medical condition being treated. A skilled artisan recognizes that the invention is useful for providing less than a complete cure, so long as one or more symptoms or signs are alleviated. For example, in treating a bladder condition, a therapeutically effective amount would include the amount that facilitates any or all of the following: decrease (or by inhibition, an increase) in cell proliferation; reduction in pain, urgency, or frequency of urination; reduction in the amount, degree and/or intensity of thinning and/or ulceration of the bladder epithelial lining; and so forth.

The term "urinary bladder" as used herein refers to a distensible membranous sac that serves for the temporary retention of the urine of an individual. Normally it resides in the pelvis in front of the rectum, and it receives the urine from the two ureters, discharging it at intervals into the urethra through an orifice closed by a sphincter. The organ is lined with transitional hypoblastic epithelium.

The term "urinary bladder antiproliferative factor" as used herein refers to an antiproliferative factor as described herein that is associated primarily with the urinary bladder. It may be associated with a cell of the bladder, such as with an epithelial cell, and this then may be referred to as a "urinary bladder epithelial cell antiproliferative factor". The factor may be identified within one or more bladder epithelial cells or it may be identified following secretion from one or more cells, or both. In addition, or alternative to, the factor may be suspended in urine within a bladder or in urine excreted therefrom, or both. Such an association of the factor with the urinary bladder may permit the detection of the APF as diagnostic for a bladder condition, such as interstitial cystitis, for example. Although in some embodiments APF is located in the urinary bladder, in alternative embodiments the APF molecule is also associated with serum, plasma, or other tissue.

II. The Present Invention

Negative growth factors are thought to be important for normal contact inhibition of eukaryotic cells, and a decrease in their activity has been associated with malignant cell growth. However, abnormally increased production of growth inhibitors has been implicated in only a few human disease states, including bone marrow failure (aplastic anemia and myelodysplastic syndrome), nontoxic goiter, chronic venous ulcers, ischemic manifestations associated with systemic sclerosis and delayed healing of gastric ulcers. In specific embodiments of the present invention, additional diseases are also caused by inappropriate inhibition of cell proliferation required for maintaining normal tissue integrity, which in solid tissues may be manifest as thinning or absence of specific cell layers and disruption of normal tissue architecture. One such class of diseases may include bladder disorders, such as interstitial cystitis.

Approximately one million people in the United States suffer from interstitial cystitis, a chronic painful urinary bladder disorder characterized by thinning or ulceration of the bladder epithelial lining; its etiology is unknown. As described herein, the present invention is directed to a novel glycosylated frizzled-related peptide inhibitor of cell proliferation that is secreted specifically by bladder epithelial cells from patients with this disorder. This antiproliferative factor (APF) profoundly inhibits bladder cell proliferation via regulation of cell adhesion protein and growth factor production. The structure of APF was deduced using ion trap mass spectrometry, enzymatic digestion, lectin affinity chromatography, and total synthesis, and confirmed by coelution of native and synthetic APF derivatives on microcapillary LC/MS. The standard form of APF was determined to be an acidic, heat stable sialoglycopeptide whose peptide chain has 100% homology to the putative 6th transmembrane domain of frizzled 8. Both synthetic and native APF had identical biological activity in normal bladder epithelial cells and T24 bladder cancer cells. Northern blot analysis indicated binding of a probe containing the sequence for the frizzled 8 segment with mRNA extracted from cells of patients with interstitial cystitis but not controls and antibodies raised against synthetic APF peptide bound to purified native APF in a dose-dependent manner. APF is therefore the first frizzled-related peptide growth inhibitor shown to contain exclusively a transmembrane segment of a frizzled protein, and is a potential biomarker for interstitial cystitis.

The reported results demonstrate that the APF made specifically by bladder epithelial cells explanted from patients with interstitial cystitis is a uniquely modified frizzled 8-related sialoglycopeptide with a peptide structure that bears 100% homology to the sixth transmembrane segment of this G-protein-coupled Wnt ligand receptor (Saitoh et al., 2001). In some embodiments of the present invention, this small secreted frizzled-related peptide is normally expressed in human bladder epithelial cells during embryogenesis, and in an alternative embodiment it is an abnormal variant of a frizzled protein that is produced only by bladder epithelial cells from these patients. However, its specificity for this disorder as well as its identification as a secreted frizzled-related peptide growth inhibitor indicates its role in the pathogenesis of this disease. Identification of APF also allows for the possible development of treatment for interstitial cystitis based on inhibition of APF production or activity, or stimulation of APF breakdown. In addition, exclusive expression of APF in adults by bladder epithelial cells from interstitial cystitis patients in some embodiments provides a direct non-invasive diagnostic test for this disorder.

To date, two disease states have been noted to be associated with abnormally increased expression of secreted frizzled-related proteins other than APF: overload-induced heart failure, in which mRNA for two such proteins have been shown to be elevated in failing ventricles as compared to control hearts (Schumann et al., 2000), and degenerative retinal disease, in which a secreted frizzled-related protein and its mRNA expression are greatly elevated (Jones et al., 2000). The previously identified secreted frizzled-related proteins contain a cysteine-rich extracellular domain, allowing them to inhibit Wnt signaling by one of two mechanisms: by binding to the Wnt ligand, or by forming nonsignalling dimers with frizzled receptors (Bafico et al., 1999). APF is therefore the first frizzled-related growth inhibitor that bears homology only to a transmembrane portion of a frizzled receptor, suggesting that growth inhibition by frizzled-related proteins may also occur via additional mechanisms. APF is also the smallest secreted frizzled-related peptide identified to date, with previously described frizzled-related peptides having molecular weights of 33.5-39.9 kDa (Jones and Jomacy, 2002).

Microarray analysis previously indicated that APF decreases the expression of several genes including Jun N-terminal kinase in bladder epithelial cells (Keay et al., 2003), suggesting the possibility that APF may interfere with non-canonical Wnt signaling mediated via a frizzled receptor protein (Pandur et al., 2002). However, linkage of the cytoskeleton to its substratum includes binding of the actin-catenin complex to E-cadherin, a protein whose expression has also been shown to be significantly upregulated by APF in bladder epithelial cells (Keay et al., 2003), and which is known to inhibit canonical Wnt signaling in both urothelial carcinoma and normal urothelial cells in vitro (Thievessen et al., 2003). Not to be bound to any theory, thus, in specific embodiments APF mediates its antiproliferative effects via inhibition of canonical or non-canonical Wnt pathway(s) in either bladder carcinoma or normal bladder cells, for example.

Although other potent sialylated small glycopeptide growth inhibitors have been isolated from serum or brain of normal mammals and shown to inhibit proliferation of both normal and malignant cells from a variety of tissues (Auger et al., 1989; Moos et al., 1995), no structural data are available for any of these natural growth inhibitors and their relationship to frizzled-related proteins or any specific signaling pathway(s) has not been determined. APF is therefore the first of this class of growth inhibitors to be completely characterized as well as the first to be synthesized. The requirement of the α-O-linked N-acetylhexosamine structure for antiproliferative activity and regulation of growth factor production by APF suggests that APF may bind to a specific cellular receptor(s), as suggested for another sialoglycopeptide growth inhibitor (Sharifi and Johnson, 1987). The extremely hydrophobic nature of the peptide moiety of APF further suggests the possibility that it may interact with the plasma membrane and expose a distinct conformation of the sugar moiety at the cell surface.

III. Antiproliferative Factor (APF)

The present invention encompasses compositions and methods associated with antiproliferative factor (APF). APF comprises a glycopeptide that inhibits proliferation of bladder epithelial cells, skin fibroblasts, and other epithelial cells including prostate cells, and in some embodiments is generated by bladder epithelial cells, such as those associated with interstitial cystitis. In particular embodiments, the compound is present in the urine of individuals having interstitial cystitis. In other embodiments, the compound is generated or biosynthesized by tissues and cells other than urinary bladder tissue and cells. In one aspect of the invention, the compound is considered a toxin, a negative growth factor, or both.

APF was identified because of its ability to inhibit the growth of cells that line the bladder wall, in specific embodiments by altering the production of several proteins by these cells, such as specific growth factors and cell adhesion proteins. Not to be bound to any theory, in further embodiments, APF causes interstitial cystitis in which the bladder lining is generally thin and/or ulcerated.

Figure 4:
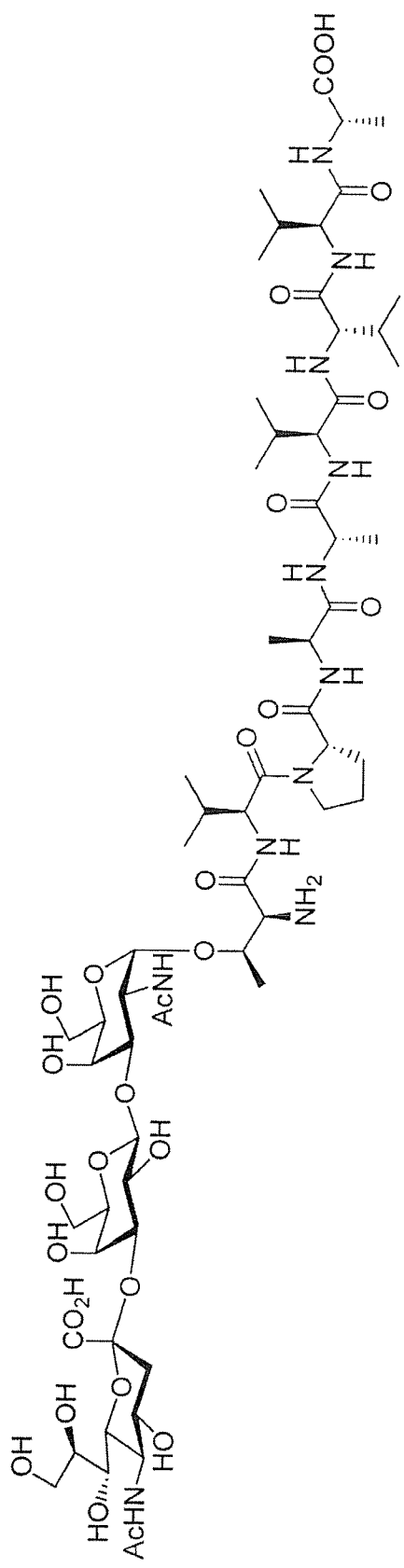
FIG. 4 illustrates one embodiment of the structure of APF, Galβ1-3GalNAcα-O-TVPAAVVVA (SEQ ID NO:25).

Thus, as used herein the term "APF" refers to a class of compounds wherein the structure in FIG. 4 is merely the prototypical APF and other related compositions are encompassed, so long as they are diagnostic for a bladder condition and/or are useful as a direct or indirect target to treat a disorder associated with abnormally increased cell proliferation, and their inhibitors are useful for treating disorders associated with decreased cell proliferation.

Although in particular aspects of the invention APF comprises the structure provided in FIG. 4, this is merely one embodiment of the invention. A skilled artisan recognizes that the structure in FIG. 4 may be secreted by bladder epithelial cells and is therefore diagnostic of a bladder disorder such as interstitial cystitis. However, in some embodiments a similar but non-identical structure of APF is diagnostic of a bladder disorder. APF compositions herein encompass both isolated natural APF, synthetic versions thereof, derivatives thereof, or a mixture thereof. Furthermore, the compounds of the present invention may be made using synthetic means or isolated from a natural source, such as bladder epithelial cells, their extracellular medium, tissue or bodily fluids such as urine, serum, or plasma.

Furthermore, inhibition of a molecule having the structure of APF in FIG. 4 is useful for the invention, but inhibition of a molecule having a similar structure of APF may also be useful. The inhibition may be directed to inhibiting the function of APF, such as with an antibody, for example; or for inhibiting the production of APF, such as an anti-sense oligonucleotide or small interfering RNA, for example; or for stimulating the breakdown of APF; or a combination thereof.

Thus, in specific embodiments, compositions related to the present invention comprise about one to about six sugar residues; and a peptide of about two to about fifteen amino acid residues, wherein the peptide-linked to one of the sugar moieties at a linking amino acid, wherein the linking amino acid comprises a heteroatom which serves as the linking portion of the linking amino acid. More specifically, the linking amino acid comprises a serine, a threonine, or a cysteine. In other specific embodiments, the compositions of the present invention comprises two or three sugar residues and nine amino acids and the linking amino acid is a threonine or serine.

In one particular aspect of the invention, an APF composition may comprise in part a hydrophobic moiety, such as a peptide, for example one including SEQ ID NO:1, SEQ ID NO:3, or SEQ ID NO:4, SEQ ID NO:5, or a lipid. The peptide may comprise at least part of a transmembrane domain, and in particular embodiments it comprises part of frizzled 8, such as a transmembrane domain of frizzled 8. In specific embodiments, the peptide is hydrophobic.

The glycoprotein comprising a galactose covalently linked to an N-acetylglucosamine or an N-acetylgalactosamine covalently linked to a peptide of SEQ ID NO:1 (SEQ ID NO:15 or SEQ ID NO:11, respectively) or variants thereof is provided herein. The term "variants thereof" includes peptidomimetics of various types (Ahn et al., 2002). The peptides may comprise any suitable amino acids, such as L-amino acids, D-amino acids, N-methylated amino acids, or a combination thereof, as well as peptidomimetic compounds such as unnatural amino acids or other "peptide-like" organic constructs that mimic the specific structural elements of a linear, cyclic, or branched peptide that correspond to active peptides. The sugar moieties may be natural, synthetic, carbohydratemimetic, or a mixture thereof may be used in a composition. Glycopeptidomimetic compounds where the sugars are carbohydratemimetic moieties or the peptide components are peptidomimetic moieties, or a combination of the two, are encompassed in the invention. In specific embodiments, the sugars of the present invention include amino sugars.

In a particular aspect of the invention, the APF has a molecular mass of 1482.8 and comprises nine amino acids and three sugar moieties in the following order: (a) Sialic acid-galactose-N-acetylgalactosamine-threonine-valine-proline-alanine-ala-nine-valine-valine-valine-alanine (SEQ ID NO:26); or (b) Sialic acid-galactose-Nacetylglucosamine-threonine-valine-proline-alanine-alanin-e-valine-valine-valine- alanine (SEQ ID NO:27); or (c) Sialic acid-gal acto se-N- acetylglucosamine- serine-leucine-proline-alanine-alanine--valine-valine-valine-alanine (SEQ ID NO:28). The composition may be further defined as having one or more of the following: the sialic acid in (a) is linked to galactose via a 2,3 linkage; the sialic acid in (b) is linked to galactose via a 2,3 linkage; the sialic acid in (c) is linked to galactose via a 2,3 linkage; the galactose in (a) is linked to the N-acetylgalactosamine via a 1,3 linkage; the galactose in (b) is linked to the N-acetylglucosamine via a 1,4 linkage; the galactose in (c) is linked to the N-acetylglucosamine via a 1,4 linkage; the N-acetylglucosamine is linked to serine via an O linkage in an alpha configuration; or the N-acetylgalactosamine is linked to threonine or serine via an O linkage in an alpha configuration.

It is contemplated that the compounds of the present invention may be modified so as to improve certain characteristics, such as solubility by adding a water soluble unit. The term "water soluble unit" means any functional group imparting water solubility, including, but not limited to, $SO_3{-}$, $PO_3^{2-}$, $CH_2 COO^-$, a quaternary ammonium group attached via an ester or alkyl linkage such as $C{=}O(CH_2)_x NAlk_3$ or $(CH_2)_x NAlk_3$ where $Alk_3$ represents three alkyl groups that are independently C1-C4 alkyl and x is 1-4, $(CH_2 CH_2 O)_n CH_2 CH_2 OX$ (n=1-3) wherein X may be H or $CH_3$, i.e., PEG or MeO-PEG. The counterion for water soluble units bearing a charge include, but are not limited to, metals such as alkali and alkaline earth metals, and halogens.

Certain compounds of the present invention comprise a threonine, a serine, or a cysteine at the N-terminus or any functional equivalent. Non-limiting examples of functional equivalents include a synthetic derivative having a primary or secondary or tertiary alcohol, an ester, a carboxylic acid, an ether, a thiol, a thiolate, or any functional group enabling for covalent linkage with a sugar molecule, provided the molecule retains biological function.

Other functionalities contemplated in "derivatives" of the present invention include isomers of any of the sugars or amino acids, whether positional, structural, or stereoisomers. Other substituents known to those skilled in the chemical arts may be provided, so long as the biological function of the molecule is retained.

IV. Diagnostic Embodiments

In specific embodiments of the present invention, APF compounds of the present invention are utilized to diagnose one or more bladder disorders.

In specific aspects of the invention, identification of an APF compound for an individual indicates an increased risk for developing a particular bladder disorder, and in some cases the symptoms of the disease may not yet be apparent. Thus, in some embodiments, the invention encompasses identifying a predisposition to developing a bladder condition, such as interstitial cystitis, or it encompasses identifying the presence of the disease.

In specific embodiments of the invention, the diagnosis of a bladder disorder comprises detection of APF glycopeptide or its activity, and the detection may be direct detection of the APF molecule or indirect detection, such as of an intermediate, a by-product, a breakdown product, a derivative, and so forth. The detection of APF may employ any suitable means in the art, although in specific embodiments the detection utilizes an antibody to the peptide, sugar, or glycopeptide moiety of APF; techniques such as mass spectrometry, nuclear magnetic resonance, or proteomic methods to detect the peptide, sugar, or glycopeptide moiety of APF; or assays for inhibition of normal or malignant cell metabolism or proliferation to detect APF activity, for example. In general, assays used to detect the peptide moiety of APF in a sample derived from an individual are well-known to those of skill in the art and include western blot analysis, ELISA assays, "sandwich" assays, radioimmunoassay, immunohistochemistry or other antibody-based assays (see, e.g., Coligan et al., Current Protocols in Immunology 1(2), Chapter 6, (1991)). Generally, Western blotting is a technique for blotting proteins or peptides onto nictrocellulose, nylon or other transfer membrane after they have been resolved by gel electrophoresis. The proteins can be detected by one of several methods, including autoradiography (if labeled), or through binding to labeled, $^{125}$I-labeled or enzyme-linked antibodies, lectin or other specific binding agents, for example.

An ELISA assay initially comprises preparing an antibody specific to the antigen, wherein the antigen comprises the peptide moiety, the sugar moiety, or the glycopeptide of APF, and this is preferably a monoclonal antibody. Next, a reporter antibody typically is prepared against the monoclonal antibody. To the reporter antibody is attached a detectable reagent such as a radioactive moiety, fluorescent moiety or enzyme, such as horseradish peroxidase or alkaline phosphatase. A sample is removed from the host and incubated on a solid support, e.g., a polystyrene dish, binding the proteins in the sample. Any free protein binding sites on the dish are then blocked by incubating with a non-specific protein, such as bovine serum albumen or milk proteins. Next, the antibody is incubated in the dish during which time the antibodies attach to any peptide moieties, the sugar moieties, or the glycopeptide moieties of APF from the sample attached to the polystyrene dish. All unbound antibody is washed out with buffer. The reporter antibody is then placed in the dish resulting in binding of the reporter antibody to any monoclonal antibody bound to the peptide moiety of APF. Unattached reporter antibody is then washed out, and the peptide moiety, the sugar moiety, or the glycopeptide of APF is then detected. Alternatively, the anti-APF antibody may be directly labeled, as above. In specific embodiments, the amount of APF present in a given volume of a patient sample is proportional to the detection of the peptide moiety, the sugar moiety, or the glycopeptide thereof and is compared against a standard curve.

A "sandwich" assay is similar to an ELISA assay. In a "sandwich" assay, the peptide moiety, the sugar moiety, or the glycopeptide of APF is passed over a solid support and allowed to bind to antibody attached to the solid support. A second antibody is then allowed to bind to the peptide moiety, the sugar moiety, or the glycopeptide of APF. A third antibody specific to the second antibody is then passed over the solid support and binds to the second antibody, which is thereby detected. Alternatively, the second antibody may be directly labeled, as above.

V. Therapeutic Embodiments

A skilled artisan recognizes that the APF compositions of the present invention may be addressed in a variety of ways to provide therapy for a bladder condition. For example, in therapeutic embodiments wherein proliferation is desirable, such as with interstitial cystitis, an inhibitor of APF activity or production, or a stimulator of APF breakdown, may be employed for therapy. In therapeutic embodiments wherein proliferation is undesirable, an APF composition may be employed for therapy.

In one aspect of the invention, a deleterious bladder condition is associated either indirectly or directly with reduced cellular proliferation, such as inhibited epithelial cellular proliferation. Such a condition may result in harmful alterations to the bladder epithelium such that it would be beneficial to reduce or substantially remove the inhibition of cellular proliferation. In these aspects, it is desirable to deliver to the individual with the bladder condition, such as deliver systemically to the individual or directly to bladder epithelium, an inhibitor of an APF composition. Specific examples of APF inhibitors include antibodies to the peptide moieties of the APF composition, as well as oligonucleotides, small interfering RNAs, small compounds that block the interaction of APF with its target, and compounds that cause or stimulate the breakdown of APF, and/or a mixture thereof. The composition may be delivered by any suitable means, although in specific embodiments it is delivered via catheter, orally, intravenously, topically, subcutaneously, transcutaneously, intramuscularly, intra-jointly, parenterally, peritoneally, intranasally, intravesically or by inhalation. In other specific embodiments, the composition is comprised in a pharmaceutically acceptable excipient, such as an aqueous or non-aqueous liquid. In particular aspects of the invention, it is administered in a non-aqueous excipient due to the hydrophobic nature of the peptide moiety. It may be delivered alone or in a carrier, such as a liposome, encapsulated cell, viral vector, nanoparticles, biodegradable gel or polymer, implanted osmotic pump, or other suitable devices.

In another aspect of the invention, a deleterious bladder condition is associated either indirectly or directly with increased cellular proliferation, such as increased epithelial cellular proliferation. Such a condition may result in malignancy of the bladder epithelium, such that it would be beneficial to reduce in part or substantially in full the amount of cellular proliferation. In these aspects, it is desirable to deliver to the individual with the bladder condition, such as deliver an APF composition systemically to the individual or directly to bladder epithelium, an APF composition. The composition may be delivered by any suitable means, although in specific embodiments it is delivered via catheter, orally, intravenously, topically, subcutaneously, transcutaneously, intramuscularly, orally, intra-jointly, parenterally, peritoneally, intranasally, intravesically or by inhalation. In other specific embodiments, the composition is comprised in a pharmaceutically acceptable excipient. It may be delivered alone or in a carrier, such as a liposome, encapsulated cell, viral vector, nanoparticles, biodegradable gel or polymer, implanted osmotic pump, or other suitable devices.

In a particular embodiment, an APF composition of the present invention may be administered to an individual with any kind of cancer, including epithelial cancers. In specific embodiments, there is a malignancy of the bladder epithelium, which may be referred to herein as bladder cancer. In specific embodiments, there is a cancer therapy additional to the APF treatment, such as gene therapy, chemotherapy, radiation, surgery, immunotherapy, or a combination thereof.

VI. Bladder Disorders

Although the present invention may be useful for any medical condition for which APF provides therapy, in specific embodiments the present invention is useful for one or more bladder disorders. Although the term "bladder disorder" refers to any abnormal condition of the urinary bladder, in specific embodiments the bladder disorder comprises interstitial cystitis, bladder cancer, either as a primary or secondary cancer, chronic pelvic pain syndrome, irritable bladder syndrome, urethral syndrome, painful bladder syndrome, chronic nonbacterial prostatitis, and other bladder conditions, for example.

In specific embodiments of the present invention, there are methods and compositions related to interstitial cystitis. Typical symptoms of interstitial cystitis include pain, which can be in the abdominal, urethral or vaginal area and is also frequently associated with sexual intercourse; urgency, which includes the sensation of having to urinate immediately and may also be accompanied by pressure and/or spasms; and increased frequency of urination, which can be day and/or night frequency of urination.

Diagnosis of interstitial cystitis is heretofore performed using cystoscopy, and hydro-distention and biopsies are normally performed at the same time. Examination by cytoscopy of a typical bladder having interstitial cystitis may identify submucosal pinpoint hemorrhages (glomerulations), thinning of the epithelium and/or Hunner's ulcers; in some cases, inflammation may also be present. Thus, there is considerable pain when urine enters into the bladder of an IC patient, making it very difficult for patients with interstitial cystitis to be able to hold urine in their bladder, due to the burning, stinging and pain.

Current therapies include oral medications, such as Elmiron, Amitriptyline (Elavil) Atarax, Neurontin, Ditropan, Prozac, Cimetidine. In specific embodiments of the invention, therapeutic agents associated with the present invention are used either alone or in conjunction with one or more of these or similar medications. In specific embodiments, the patients also suffer with various other syndromes including fibromyalgia, urethral syndrome, vulvodynia, irritable bowel syndrome, chronic fatigue syndrome, allergies, and other auto-immune disorders, such as scleroderma.

VII. Pharmaceutical Compositions

The present invention is also directed to pharmaceutical compositions for use in treating or ameliorating bladder conditions, such as interstitial cystitis, bladder cancer, epithelial hyperplasia or malignancies of epithelial origin, of fibroblast hyperplasia or malignancy, other solid tumors, or lymphoreticular malignancies. The compounds of the present invention are also contemplated for use as an adjuvant treatment for bladder cancer or other malignancies, as an antiangiogenic agent or an antifungal agent. It is further contemplated that the compounds of the present invention may be used to generate antibodies, antisense oligonucleotides, small interfering RNA, or agents that block the interaction of APF with its target for the treatment of interstitial cystitis or other disorders related to cell proliferation.

Such methods generally involve administering a pharmaceutical composition comprising an effective amount of the glycopeptides of the present invention. Other exemplary compositions include an effective amount of an oligonucleotide encoding the nonapeptide of a sequence as essentially set forth in SEQ ID NO:1, SEQ ID NO:3, SEQ ID NO:4, SEQ ID NO:5, or a small interfering RNA comprising part or all of a sequence encoding peptides as set forth in SEQ ID NO:1, SEQ ID NO:3, SEQ ID NO:4, or SEQ ID NO:5, for example.

Where the invention is directed to treating with the compounds of the present invention, administration of the compounds of the invention with a suitable pharmaceutical excipient as necessary can be carried out via any of the accepted modes of administration. The compounds may be comprised in a pharmaceutically acceptable excipient, which may be considered as a molecular entity and/or composition that does not produce an adverse, allergic and/or other untoward reaction when administered to an animal, as appropriate. It includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated.

Thus, administration can be, for example, intravenous, topical, subcutaneous, transcutaneous, intramuscular, oral, intra-joint, parenteral, peritoneal, intranasal, intravesical or by inhalation. Suitable sites of administration thus include, but are not limited to, skin, bronchial, gastrointestinal, anal, vaginal, eye, bladder, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., REMINGTON'S PHARMACEUTICAL SCIENCES, 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Remington's Pharmaceutical Sciences, supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person. However, it is possible that an effective dose of APF, especially if administered directly into the bladder, may be outside of this range.

Stability of the conjugate can be further controlled by chemical alterations, including D amino acid residues in the polypeptide chain as well as other peptidomimetic moieties. Furthermore, stability of the conjugates could also be enhanced by unnatural carbohydrate residues.

VIII. Combination Treatments

In order to increase the effectiveness of an APF composition for the treatment of cancer in an individual, such as a patient, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy, for example, by combining it with other cancer therapies. In the context of the present invention, it is contemplated that APF composition therapy could be used similarly in conjunction with chemotherapeutic, radiotherapeutic, surgical, or immunotherapeutic intervention, in addition to other pro-apoptotic or cell cycle regulating agents.

Alternatively, the APF treatment may precede, follow, or both the other agent treatment by intervals ranging from minutes to weeks. In embodiments where the APF composition and the other agent are applied separately to a cell of the individual, one would generally ensure that a significant period of time did not expire between the time of each delivery, such that the APF composition and the other agent would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, for example, wherein the APF treatment is "A" and the secondary agent, such as radio- or chemotherapy, is "B":

A/B/A B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the APF compositions of the present invention to a patient will follow general protocols for the administration of chemotherapeutics, taking into account the toxicity, if any, of the molecule. It is expected that the treatment cycles would be repeated as necessary. It also is contemplated that various standard therapies, as well as surgical intervention, may be applied in combination with the described hyperproliferative cell therapy.

A. Chemotherapy

A skilled artisan recognizes that in addition to the APF treatment described herein for the purpose of inhibiting cell growth, other chemotherapeutic agents are useful in the treatment of neoplastic disease. Examples of such chemotherapeutic agents include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with APF therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a secondary gene therapy in which a second therapeutic polynucleotide is administered before, after, or at the same time as an APF molecule, having a combined anti-hyperproliferative effect on target tissues. A variety of proteins are encompassed within the invention, including inhibitors of cellular proliferation, such as tumor suppressors, including p53; and/or regulators of programmed cell death, such as Bcl-2.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IX. Kits

Diagnostic and/or therapeutic kits associated with the glycoproteins of the present invention comprise another aspect of the present invention. Such kits will generally contain, in suitable container means, an APF molecule of the present invention, such as a glycoprotein comprising a peptide having a sequence as, for example, but not limited to, one essentially set forth in SEQ ID NO:1, SEQ ID NO:3, SEQ ID NO:4, or SEQ ID NO:5, or a means to detect such as molecule. The kit may have a single container means that contains the APF composition or it may have distinct container means for the APF composition and other reagents that may be included within such kits. Other kits may comprise inhibitors of APF in suitable container means, such as antibodies, small interference RNAs, and so forth. Diagnostic kits may comprise any suitable reagents to identify an APF composition, such as antibodies, for example.

The components of the kit may be provided as liquid solution(s), or as dried powder(s). When the components are provided in a liquid solution, the liquid solution is an aqueous or non-aqueous solution, with a sterile aqueous or non-aqueous solution being particularly preferred. When reagents or components are provided as a dry powder, the powder can be reconstituted by the addition of a suitable solvent. It is envisioned that the solvent may also be provided in another container means.

Kits may comprise reagents for detecting peptides having a sequence as essentially set forth in SEQ ID NO:1, SEQ ID NO:3, SEQ ID NO:4, or SEQ ID NO:5, such as is required for immunoassay. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, a number of exemplary labels are known in the art and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably aliquoted. Where a second binding ligand is provided, the kit will also generally contain a second vial or other container into which this ligand or antibody may be placed. The kits of the present invention will also typically include a means for containing the antibody, antigen, and reagent containers in close confinement for commercial sale. Such containers may include injection or blow-molded plastic containers into which the desired vials are retained.

X. APF Antibodies

In another aspect, the present invention contemplates an antibody that is immunoreactive with a proteinaceous or sugar composition, such as a peptide, a sugar, a glycopeptide, or a combination thereof of the invention. The peptide may be comprised as part of a larger composition, such as an APF of the present invention.

An antibody can be a polyclonal or a monoclonal antibody. In a preferred embodiment, an antibody is a monoclonal antibody. Means for preparing and characterizing antibodies are well known in the art (See, e.g., Howell and Lane, 1988).

Briefly, a polyclonal antibody is prepared by immunizing an animal with an immunogen comprising a peptide, sugar or glycopeptide of the present invention, with or without an adjuvant or other such molecules that enhance immune responses (e.g. KLH) and collecting antisera from that immunized animal. A wide range of animal species can be used for the production of antisera. Typically an animal used for production of anti-antisera is a rabbit, a mouse, a rat, a chicken, a hamster or a guinea pig. Because of the relatively large blood volume of rabbits, a rabbit is a preferred choice for production of polyclonal antibodies.

Antibodies, both polyclonal and monoclonal, specific for APF peptides, sugars, glycopeptides, and particularly those represented by SEQ ID NO:1, SEQ ID NO:3, SEQ ID NO:4, or SEQ ID NO:5, variants and epitopes thereof, may be prepared using conventional immunization techniques, as will be generally known to those of skill in the art. A composition containing antigenic epitopes of APF can be used to immunize one or more experimental animals, such as a rabbit, chicken, or mouse, which will then proceed to produce specific antibodies against the peptide, sugar, or glycopeptide regions of APF. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with an APF composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired APF peptide, sugar, or glycopeptide.

Following immunization, spleen cells are removed and fused, using a standard fusion protocol with plasmacytoma cells to produce hybridomas secreting monoclonal antibodies against APF and/or APF peptides. Hybridomas which produce monoclonal antibodies to the selected antigens are identified using standard techniques, such as ELISA and Western blot methods. Hybridoma clones can then be cultured in liquid media and the culture supernatants purified to provide the APF-specific monoclonal antibodies.

It is proposed that the monoclonal antibodies of the present invention will find useful application in standard immunochemical procedures, such as ELISA and Western blot methods, as well as other procedures which may utilize antibody specific to APF epitopes.

Additionally, it is proposed that monoclonal antibodies specific to the particular peptide may be utilized in other useful applications. For example their use in immunoabsorbent protocols may be useful in purifying native or recombinant APF species or variants thereof.

In general, both poly- and monoclonal antibodies against APF may be used in a variety of embodiments. For example, they may be employed in antibody cloning protocols to obtain cDNAs or genes encoding APF or related proteins. This may also be used to select for hybridoma cells or lymphocytes that recognize the APF epitopes or make antibodies or segments thereof that recognize APF epitopes. They may also be used in inhibition studies to analyze the effects of APF in cells or animals. Anti-APF antibodies will also be useful in immunolocalization studies to analyze the distribution of APF peptides during various cellular events, for example, to determine the cellular or tissue-specific distribution of the APF peptide or glycopeptide under different physiological conditions. A particularly useful application of such antibodies is in purifying native or recombinant APF peptides or glycopeptides, for example, using an antibody affinity column. The operation of all such immunological techniques will be known to those of skill in the art in light of the present disclosure.

While the invention has been described with reference to certain particular embodiments thereof, those skilled in the art will appreciate that various modifications may be made without departing from the spirit and scope of the invention. The scope of the appended claims is not to be limited to the specific embodiments described.

The present invention also encompasses methods of generating antibodies to an APF composition, such as to a peptide moiety, a sugar moiety, and/or a glycopeptide moiety. The peptide moieties include SEQ ID NO:1, SEQ ID NO:3, SEQ ID NO:4, SEQ ID NO:5, or SEQ ID NO:6, for example. These antibodies may then be utilized for detection of a bladder condition, such as interstitial cystitis, for example; for diagnosis of a bladder condition; or for therapeutic purpose, such as to inhibit an APF composition.

XI. Screening for Inhibitors of Antiproliferative Factor

Inhibitors of APF activity can also be screened using direct or indirect cell proliferation inhibition assays, for example. In the direct assays, inhibition of normal or malignant cell proliferation by APF is abrogated in a dose-dependent manner. Cell proliferation assays, including tritiated thymidine incorporation, bromodeoxyuridine incorporation, live cell counts, or any of a number of commercially available compounds used to detect cell proliferation could be used for this purpose. In the indirect assay, inhibition of normal or malignant cell metabolism by APF is used as an indirect indication of cell proliferation; the inhibition of cell metabolism by APF would then be abrogated in a dose-dependent manner by inhibitors of APF activity.

EXAMPLE 1

Exemplary Methods and Reagents

Cell Cultures

Cystoscopy was performed under general anesthesia, and 4 mm 2 pieces of transitional epithelium with submucosa bladder tissue were obtained using rigid cold cup biopsy forceps from six patients who had previously undergone cystoscopy and fulfilled the NIDDK/NIH diagnostic criteria for interstitial cystitis, and six age- race- and gender-matched controls who were asymptomatic for urinary tract disease, as previously described (Keay et al., 2001; Keay et al., 2000; Keay et al., 2003a; Keay et al., 2003b; Keay et al., 1996). All patients were at least 18 years old and enrolled in accordance with guidelines of the Institutional Review Board of the University of Maryland School of Medicine.

Explanted epithelial cells were propagated from these biopsy specimens in DMEM-F12 (Media Tech, Hemdon, Va.) with 10% heat inactivated fetal bovine serum (FBS), 1% antibiotic/antimycotic solution, 1% L-glutamine, 1.0 U/ml insulin (all from Sigma, St. Louis, Mo.), and 5 µg/ml hEGF (R & D Systems, Minneapolis, Minn.) at 370 C in a 5% $CO_2$ atmosphere, and characterized by binding of AE-1/AE-3 pan-cytokeratin antibodies (Signet, Dedham, Mass.), as previously described (Keay et al., 2001; Keay et al., 2000; Keay et al., 2003a; Keay et al., 2003b; Keay et al., 1996).

T24 bladder carcinoma cells (ATCC #HTB 4) were purchased from the American Type Culture Collection (Rockville, Md.) and cultured in McCoy's 5A medium (Gibco-Invitrogen, Carlsbad, Calif.) containing 10% FBS, 1% glutamine and 1% antibiotic/antimycotic solution (all from Sigma).

APF Purification

APF was harvested from the supernatant of explanted patient bladder epithelial cells and purified using molecular weight fractionation, ion exchange chromatography, hydrophobic interaction chromatography, and reversed phase high performance liquid chromatography (HPLC), as previously described (Keay et al., 2000). Mock APF was prepared using the supernatant of normal control bladder epithelial cells and the same purification procedure.

Microcapillary LC-MS/MS Analysis

Microcapillary reversed-phase liquid chromatography (mRPLC) was performed using an Agilent 1100 capillary LC system (Agilent Technologies, Palo Alto, Calif.) coupled online to an ion trap mass spectrometer (LCQ Deca XP, ThermoFinnigan, San Jose, Calif.). Reversed-phase separations of each sample were performed using 75 µm i.d.×10 cm long fused silica electrospray ionization capillary columns (Polymicro Technologies, Phoenix, Ariz.) that were slurry packed in house with 3 µm, 300 Å pore size C-18 stationary phase (Vydac Hesperia, Calif.). After sample injection, the column was washed for 20 min with 98% solvent A (0.1% v/v formic acid in water) and gradient elution was conducted using a linear step gradient from 2% solvent B (0.1% v/v formic acid in acetonitrile) to 42% solvent B in 40 minutes, then from 42% to 95% B in 15 min, at a constant flow rate of 0.5 µL/min.

The ion trap mass spectrometer was operated in a data dependent mode in which each full mass spectrometry (MS) scan was followed by three tandem MS scans where the three most abundant molecular ions were dynamically selected for collision-induced dissociation (CID) using a normalized collision energy of 38%. The temperature of the heated capillary and electrospray voltage were 180° C. and 1.8 kV, respectively.

$^3$H-Thymidine Incorporation

Cell proliferation was measured by $^3$H-thymidine incorporation into explanted normal human bladder epithelial cells, as previously described (Keay et al., 2001; Keay et al., 2000; Keay et al., 2003a; Keay et al., 2003b; Keay et al., 1996). Briefly, purified native or synthetic APF (or the appropriate mock preparation) was diluted in serum-free MEM (containing only glutamine and antibiotics/antimycotics) and applied to the cells; cell controls received serum-free MEM alone. Cells were then incubated at 37° C. in a 5% $CO_2$ atmosphere for 48 hours. The cells were then labeled with 1 µCi/well $^3$H-thymidine for 4 hours, trypsinized, insoluble cell contents harvested and methanol-fixed onto glass fiber filter paper, and the amount of radioactivity incorporated determined. Significant inhibition of 3H-thymidine incorporation was defined as a mean decrease in counts per minute of greater than 2 standard deviations from the mean of control cells for each plate.

Cell Count Determination

For cell count experiments, explanted normal human bladder epithelial cells, LNCaP prostate carcinoma cells, or T24 bladder carcinoma cells were plated onto Corning 24 well tissue culture plates (VWR Scientific Products) in MEM (primary bladder cells), DMEM (LNCaP cells), or McCoy's 5A medium (T24 cells) containing 10% FBS, 1% antibiotic/antimycotic solution, 1% L-glutamine at a density of $1\times10^4$ cells/well and incubated at 37° C. in a 5% $CO_2$ atmosphere overnight. On the next day the medium was removed and replaced with serum-free MEM, DMEM, or McCoy's medium containing 1% antibiotic/antimycotic solution and 1% L-glutamine (all three cell types). HPLC-purified or synthetic APF (or their mock preparations) were then added to the medium and cells further incubated at 37° C. with 5% $CO_2$. Forty-eight hours later the culture supernatant was removed for growth factor analysis by ELISA, cells were trypsinized, stained with Trypan blue (Sigma) and counted using a hemacytometer.

ELISAs

HB-EGF—ELISAs were performed as previously described (Keay et al., 2001; Keay et al., 1998), coating 96 well Immulon II plates (Dynatech Laboratories, Chantilly, Va.) with 200λ culture supernatant at 40° C. overnight. Plates were subsequently rinsed, blocked, and anti-HB-EGF antibody (1 μg/ml) (R & D Systems, Minneapolis, Minn.) applied. Following additional incubation and rinses, biotinylated anti-goat IgG/avidin D horseradish peroxidase was added. Binding was detected by development with ABTS [2,2'-Azino-bis-(3-ethylbenzothiazoline-6-sulfonic acid)]; absorbance was read at 405 nm.

EGF—Culture supernatant (200λ)was pipetted into wells precoated with monoclonal anti-EGF antibody, according to the manufacturer's instructions (R & D Systems). Following incubation and rinses, HRP-linked polyclonal anti-EGF was added and binding detected by development with tetramethylbenzidine (TMB) substrate; absorbance was read at 450 nm.

Linear absorbance vs. concentration curves were prepared from results with known concentrations of EGF or HB-EGF, and sample concentrations were determined by plotting absorbance values.

Enzymatic Cleavage

Partially purified APF was incubated with any of three positionally-specific neuraminidases [2-3; 2-3,6; 2-3,6,8,9] (all from Sigma) at 37° C. for 2 hours; control APF was incubated under the same conditions but without enzyme. APF was then purified from enzyme by ultrafiltration using a 3000 MW cut-off Centricon filter (Amicon, Bedford, Mass.), and antiproliferative activity and lectin-binding of each ultrafiltrate determined.

Lectin Binding

HPLC purified APF or enzymatically-treated APF samples were applied to the following agarose-conjugated lectins and eluted according to the manufacturer's instructions: wheat germ agglutinin, concanavalin A, lentil lectin (all from Amersham), *Vicia villosa* (Sigma), *Erythrina cristagalli, Griffonia simplicifolia* I and II, peanut agglutinin, Jacalin lectin (all from Vector Labs, Burlingame, Calif.), or *Tritrichomonas mobilensis* lectin (Calbiochem-Novobiochem Corp., San Diego, Calif.). Eluates were tested for antiproliferative activity by the $^3$H-thymidine incorporation assay.

Sucrose Density Gradient Isoelectric Focusing

HPLC-purified APF was fractionated by high-speed electrofocusing in a pH 2 to 10 sucrose density gradient formed at 15 W for 18 hours with an LKB 8100-1 column (LKB Instruments Inc., Gaithersburg, Md.). The pH of the fractions was determined at 40° C., and antiproliferative activity of the neutralized (pH 7.0) fractions was determined in normal bladder cells using the $^3$H-thymidine incorporation assay.

APF Synthesis

The synthesis of the peptides was carried out by solid phase methods on the Nautilus 2400 synthesizer (Argonaut Technologies, Foster City, Calif.) utilizing standard Fmoc chemistry on alanyl 2-chlorotrityl resin (Calbiochem-Novobiochem). Fmoc-protected amino acids (Anaspec Inc., San Jose, Calif.) were coupled utilizing N-{(dimethylamino)-1H-1,2,3-triazolo[4,5-b]pyridin-1-ylmethylene}-N-methylmethanaminium hexafluorophosphate N-oxide (HATU) (Sigma-Aldrich, Milwaukee, Wis.) and 1-hydroxy-7-azabenzotriazole (HOAt) (Anaspec, Inc.) reagents. All other reagents were purchased from Sigma-Aldrich. All intermediates and the final products were verified by mass spectrometry.

Fmoc protected O-α-(N-acetyllactosamine)-L-Threonine. Fmoc-L-Thr (Calbiochem-Novabiochem) was converted to phenacyl ester and glycosylated with 2-azido-1-α-bromo-hexa-O-acetyl-2-deoxylactose in the presence of silver triflate according to a slight modification of the procedure by Leuck and Kunz (Leuck and Kunz, 1997). The reaction was carried out a −40° C. that ensured>98% selectivity for the α-anomer. The anomeric purity was determined by proton NMR spectroscopy. The phenacyl ester was de-protected by zinc/acetic acid/acetic anhydride, which also resulted in the simultaneous reduction of the azido group and acetylation of the resulting amino group (Svarovsky and Barchi, 2003). The final product was purified by preparative, reverse phase (C8 column) HPLC.

Fmoc protected O-β-(N-acetyllactosamine)-L-Threonine. The procedure for production of the β anomer was identical to that for production of the α anomer except that the glycosylation of threonine by 2-azido-1-α-bromo-hexa-O-acetyl-2-deoxylactose was carried out at −20° C. The product generated by this procedure was a mixture of the α (90%) and β (10%) anomers, which were readily separated by silica gel flash chromatography using an ethyl acetate/hexanes gradient.

Fmoc protected O-α-[Galβ(1->3)GalNAc]-L-Threonine. The synthetic procedure was similar to the method used to produce the Fmoc protected 0- α-(N-acetyllactosamine)-L-Threonine. Fmoc-L-Threonine phenacyl ester was glycosylated by the trichloroacetimidate-disaccharide donor in the presence of boron trifluoride diethyl etherate, following the procedure published by Qiu et al. (Qiu et al., 1996) with slight modifications. The conversion of the azido group and the deprotection of the phenacyl ester were identical to the procedures used in the Fmoc protected O-α-(N-acetyllactosamine)-L-Threonine synthesis.

General method for glycopeptide synthesis. The glycosylated Fmoc-protected threonine was activated by HATU/HOAt and added to the growing peptide chain in presence of Hunig's base for a prolonged coupling time (16 hours). The glycopeptide was cleaved from the resin with a mixture of trifluoroacetic acid, water, tri-isopropylsilane (90:5:5 v/v/v), the solvent was removed in vacuo, and the residue was dried under high vacuum. The crude, dry glycopeptide was dissolved in anhydrous methanol and treated with sodium methoxide powder for 30 min. When HPLC-MS indicated the complete removal of the acetyl groups, the reaction was stopped with acetic acid and evaporated to dryness. The crude deacetylated product was purified by preparative HPLC using a C8 reverse phase column.

Sialylation of N-terminal threonine hexosamide residue. The N-acetylhexosamine derivatives of the peptides were sialylated enzymatically using recombinant rat α-2,3 (N) sialyltransferase (EMD Biosciences, Inc., La Jolla, Calif.) and CMP-N-acetyl neuraminic acid substrate (Sigma) in 250 mM MOPS buffer pH 7.4. All crude glycopeptides were purified by reverse phase HPLC on a C8 column, and the purified peptides were analyzed by mass spectrometry.

Northern Blot Analysis

Total RNA was extracted from explanted bladder epithelial cells from 6 patients with interstitial cystitis and their age-, race-, and gender-matched asymptomatic controls using Trizol/chloroform (Gibco-BRL) extraction. Equivalent amounts of RNA from each sample were loaded onto a 1% agarose/2% formaldehyde gel, separated by standard gel electrophoresis and transferred to a nylon membrane. DIG-labeled probe for APF mRNA was prepared by random labeling using the known sequence of nucleotides 1626-1632 (accgtgcccgc-cgcggtggtggtcgcc) (SEQ ID NO:2) of human frizzled 8 protein (EMBL NM_031866; SEQ ID NO:7, for example) and the DIG Northern Starter Kit with SP6/T7/T3 RNA polymerase (Roche Applied Science, Indianapolis, Ind.); DIG-labeled probe for beta actin mRNA was purchased from Roche Applied Science (prepared using nucleotides 69-618 of human beta actin) (EMBL HSAC07). Blots were developed by chemiluminescence detection with CDP-Star (Roche Applied Science).

Anti-APF Antibodies

Figure 7:
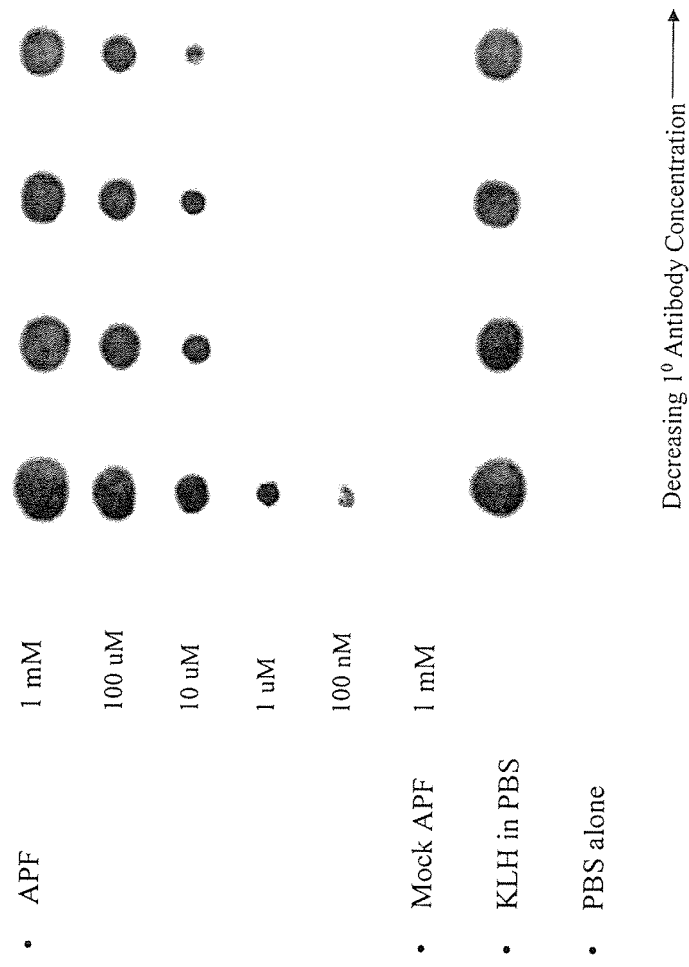
FIG. 7 demonstrates dose-dependent binding to HPLC-purified native APF of purified rabbit antibodies raised against synthetic APF.

Synthetic APF peptide was generated by preparing an APF composition comprising a peptide moiety comprised of a derivative of SEQ ID NO:1, in which an N-terminal cysteine residue was added (SEQ ID NO:6). The peptide was coupled to KLH at the cysteine residue (serving as the linking amino acid) via the sulfur atom, and injected (0.5 mg peptide/rabbit) into two New Zealand White rabbits for antibody production. Following two monthly booster injections, serum was harvested, immunoglobulin fraction purified, and its reactivity against HPLC-purified native APF and KLH tested in a dot-blot format, using HRP-conjugated goat anti-rabbit IgG for the secondary antibody. As shown in FIG. 7, these antibodies detected APF and KLH, and a standard curve against known varying concentrations of APF could be generated. Preimmune antibodies did not bind to either APF or KLH.

EXAMPLE 2

Identification of Amino Acids by Mass Spectrometric Analysis

In specific aspects of the invention, an APF molecule is identified and/or characterized by any suitable means in the art, such as through the characterization of the peptide, sugar, or glycopeptide moiety of APF. In one specific embodiment, mass spectrometry is utilized. In other embodiments, techniques such as nuclear magnetic resonance or proteomic techniques (including isotope-coded affinity assays), and sensitive chromatographic methods may be utilized, for example.

Microcapillary reversed-phase liquid chromatography was used to obtain extremely pure preparations of APF peptide for mass spectrometry. Analysis of three preparations of HPLC-purified APF using the microcapillary technique indicated the presence of three peptide peaks in approximately equal proportions in each preparation, only one of which had antiproliferative activity against primary bladder epithelial cells in vitro. Ion trap mass spectrometric analysis of the active peak indicated a molecular weight of 1482.8 Daltons (FIG. 1A). Analysis of peaks generated by collision-induced dissociation of the active substance indicated a terminal sialic acid linked to a hexose moiety, which in turn was linked to an N-acetylhexose moiety (FIG. 1B); detectable amino acid moieties present from the N terminus following further dissociation of the 827 Dalton peptide moiety included alanine-alanine-valine-valine-valine-alanine (FIG. 1C). The remaining N-terminal amino acids present had a combined molecular weight of 351.4 Daltons. Search for a gene encoding a homologous peptide indicated 100% homology between a sequence with the appropriate total molecular weight (T-V-P-A-A-V-V-V-A: SEQ ID NO:1) and amino acids 541-549 in the 6th transmembrane region of frizzled 8, a Wnt ligand receptor (Qiu et al., 1996).

The peptide moiety of the present invention may also comprise conservative variants of SEQ ID NO:1, such as, for example, a peptide comprising the amino acid sequence of S-V-P-A-A-V-V-V-A (SEQ ID NO:3); T-V-P-A-A-V-V-L-A (SEQ ID NO:4); S-L-P-A-A-V-V-V-A (SEQ ID NO:5); or C-T-V-P-A-A-V-V-V-A (SEQ ID NO:6). It is contemplated that these conservative variants include known conservative substitutions or additions, as in the case of SEQ ID NO:6, defined by chemical properties. For example, serine, threonine and cysteine comprise heteroatoms (atoms other than carbon or hydrogen having nucleophilic or electrophilic properties exploitable as linking means), specifically oxygen (O) and sulfur (S) which provides a means to link to at least one sugar moiety of the present compositions and are considered conservative variants when interchanged in the peptides and glycopeptides of the present invention. In another example, at least one or more leucines is substituted for any one of the valine subunits. The peptide moiety of the present invention may also comprise a variant of SEQ ID NO:1 comprising D-proline, such as, for example, a peptide comprising the amino acid sequence of SEQ ID NO:10 (T-V-P-A-A-V-V-V-A, wherein the P is a D-proline).

The skilled artisan is aware that amino acid substitutions can be made that do not change substantially the functionality of the peptide and/or polypeptide. Therefore, the present invention contemplates a glycopeptide comprising a peptide having a sequence essentially as set forth in SEQ ID NO: 1. The term "a sequence essentially as set forth in SEQ ID NO:1" means that the sequence substantially corresponds to a portion of SEQ ID NO:1 and has relatively few amino acids which are not identical to, or a biologically functional equivalent of, the amino acids of SEQ ID NO: 1. The term "biologically functional equivalent" is well understood in the art and is further defined in detail herein, as a protein having a sequence essentially as set forth in SEQ ID NO:1 and that is associated with a diseased state of an epithelial cell. Accordingly, sequences which have less than about 50%, between about 50% and about 65%, 70% and about 80%; or more preferably, between about 85% and about 90%; or even more preferably, between about 90 and 95% and about 99%; of amino acids which are identical or functionally equivalent to the amino acids of SEQ ID NO: 1 will be sequences which are "essentially as set forth in SEQ ID NO:1". However, in specific embodiments, the APF molecule still comprises activity by substituting more than one amino acid and may still be active. For example, the entire peptide may be substituted with derivatized amino acids or peptidomimetic agents, which may be hydrophobic, or another hydrophobic moiety, such as a lipid.

Biological Functional Equivalents

Modification and changes may be made in the structure of the peptides of the present invention or DNA segments which encode them and still obtain a functional molecule that encodes a protein or peptide with desirable characteristics.

The following is a discussion based upon changing the amino acids of a protein to create an equivalent, or even an improved, second-generation molecule. The amino acid changes may be achieved by changing the codons of the RNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and messenger RNA sequence, and nevertheless obtain a protein with like properties. It is thus contemplated by the inventors that various changes may be made in the peptide sequences of the disclosed compositions, or corresponding DNA or RNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within .+−0.2 is preferred, those which are within .+−0.1 are particularly preferred, and those within .+−0.05 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within +1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

It will also be understood that amino acid sequences may include additional residues, such as additional N- or C-terminal amino acids and yet still be essentially as set forth in one of the sequences disclosed herein, so long as the sequence meets the criteria set forth above, including the maintenance of biological protein activity where protein expression is concerned. The addition of terminal sequences particularly applies to sequences, which may, for example, include various unnaturally occurring amino acid sequences flanking either of the N- or C-termini to allow for facile covalent linkage to another molecule, i.e., a sugar residue.

EXAMPLE 3

Identification of Sugar Moieties by Lectin Binding Analysis

In specific aspects of the invention, an APF molecule is identified and/or characterized by any suitable means in the art. In one specific embodiment, lectin binding analysis is utilized to identify sugar moieties. Other methods for sugar identification including, but not limited to, chemical degradation, NMR spectroscopy, mass spectrometry, and antibody binding can also be used to identify sugar moieties.

To determine the identity and linkage of the hexose and hexosamine moieties, HPLC-purified APF was incubated in its native state with various agarose-conjugated lectins and the eluates tested for antiproliferative activity (Table 2).

TABLE 2

Lectin Binding Analysis

| Lectin | Reported Specificity | Native | APF Binding Neuraminidase-treated |
|---|---|---|---|
| Wheat germ agglutinin | sialic acid; terminal GlcNAc | + | ND |
| Tritrichomonas mobilensis | sialic acid | + | ND |
| Peanut agglutinin | Gal$\beta$1-3GalNAc; Galactose | − | + |
| Concanavalin A | Mannose, Glucose | − | − |
| Lentil lectin | Mannose, Glucose; terminal GlcNAc | − | − |
| Vicia villosa | Terminal GalNAc; Gal$\alpha$1-3GalNAc | − | − |
| Griffonia simplicifolia I | Galactose; GalNAc | − | + |
| Griffonia simplicifolia II | Terminal GlcNAc | − | − |
| Jacalin | GalNAc; Galactose | − | + |
| Erythrina cristagalli | Gal$\beta$1-4GlcNAc; Galactose | − | + |

Figure 2:
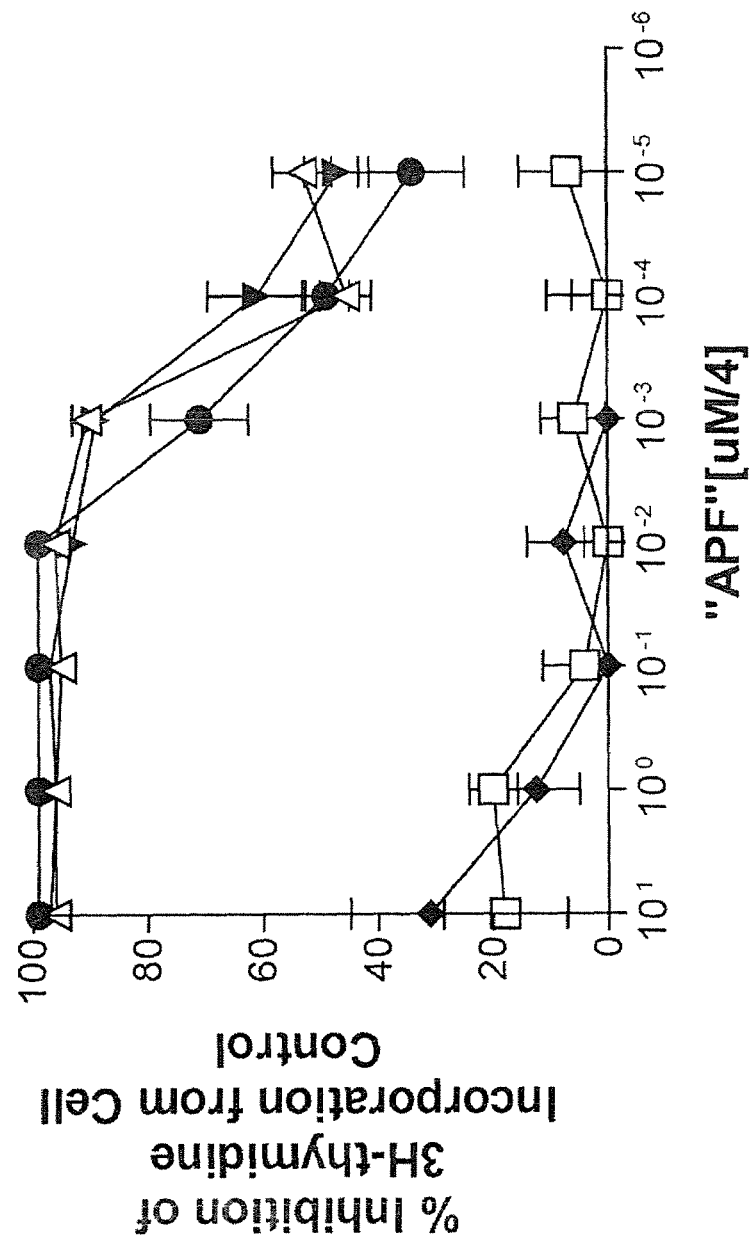
FIG. 2 demonstrates antiproliferative activity of APF peptide and glycosylated derivatives. Inhibition of primary normal bladder epithelial cell $^3$H-thymidine incorporation by synthetic APF and its derivatives. Equimolar quantities of the peptide backbone alone (-□-), N-acetyllactosamine-α-O-Thr derivative (closed -▼-), sialylated N-acetyllactosamine-α-O-Thr derivative (-Δ-), N-acetyllactosamine-β-O-Thr derivative (closed -◆-), and Galβ1-3GalNAc-α-O-Thr derivative (closed -•-), were applied to normal bladder epithelial cells, and $^3$H-thymidine incorporation was determined and compared to incorporation in cells grown in medium containing buffer alone. All specimens were assayed in triplicate in 2-3 repeated experiments; data are expressed as the mean inhibition of incorporation, and vertical lines indicate standard error of the mean.
Figure 3A:
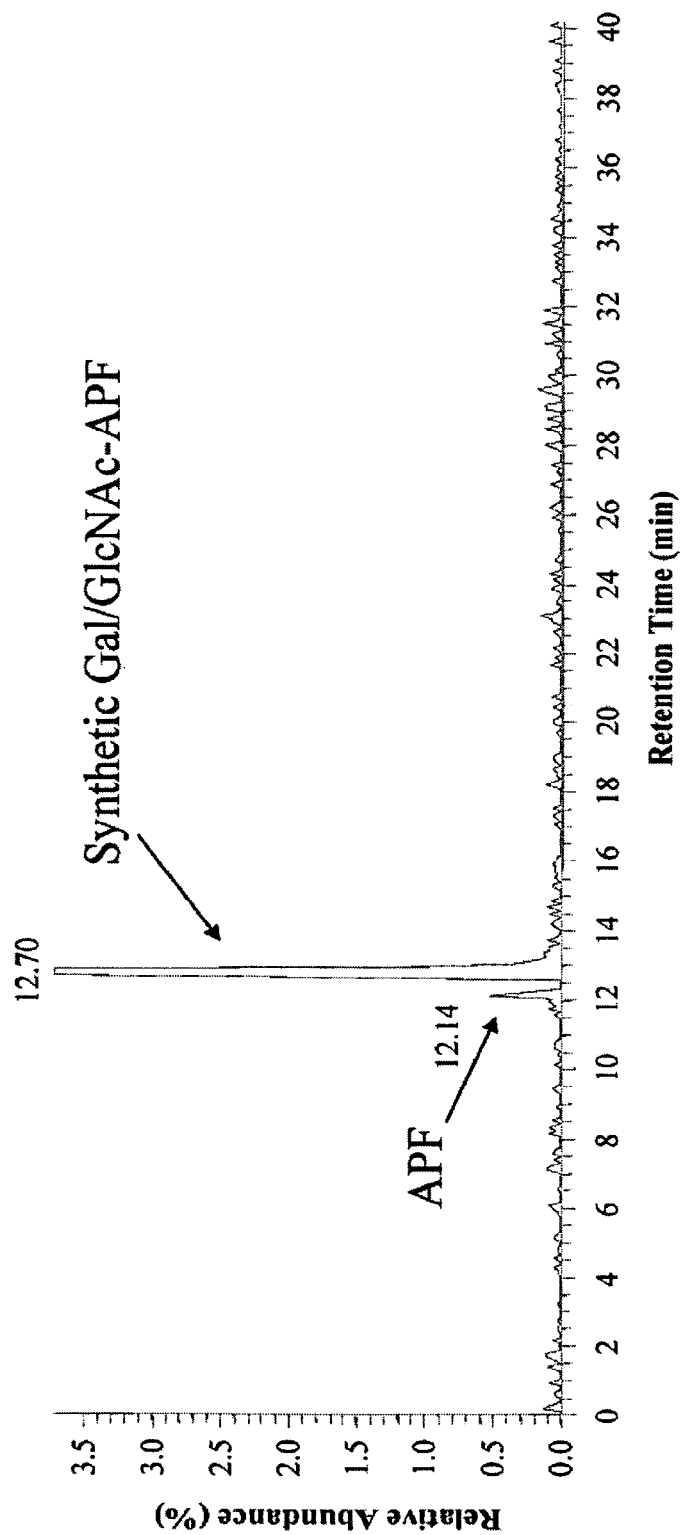
FIGS. 3A and 3B provide microcapillary reversed-phase liquid chromatography of native APF, and synthetic GlcNAc (also referred to as Gal β1-4GlcNAcα-O-TVPAAVVVA, wherein such glycosylated peptide is SEQ ID NO:24) and GalNAc (also referred to as Gal β1-3GalNAcα-O-TVPAAV-VVA, wherein such glycosylated peptide is SEQ ID NO:25, in some embodiments) derivatives. Neuraminidase-treated APF was injected along with either synthetic GalGlcNAc-containing APF or synthetic GalGalNAc-containing APF and their relative mobilities on C18 determined.
Figure 3B:
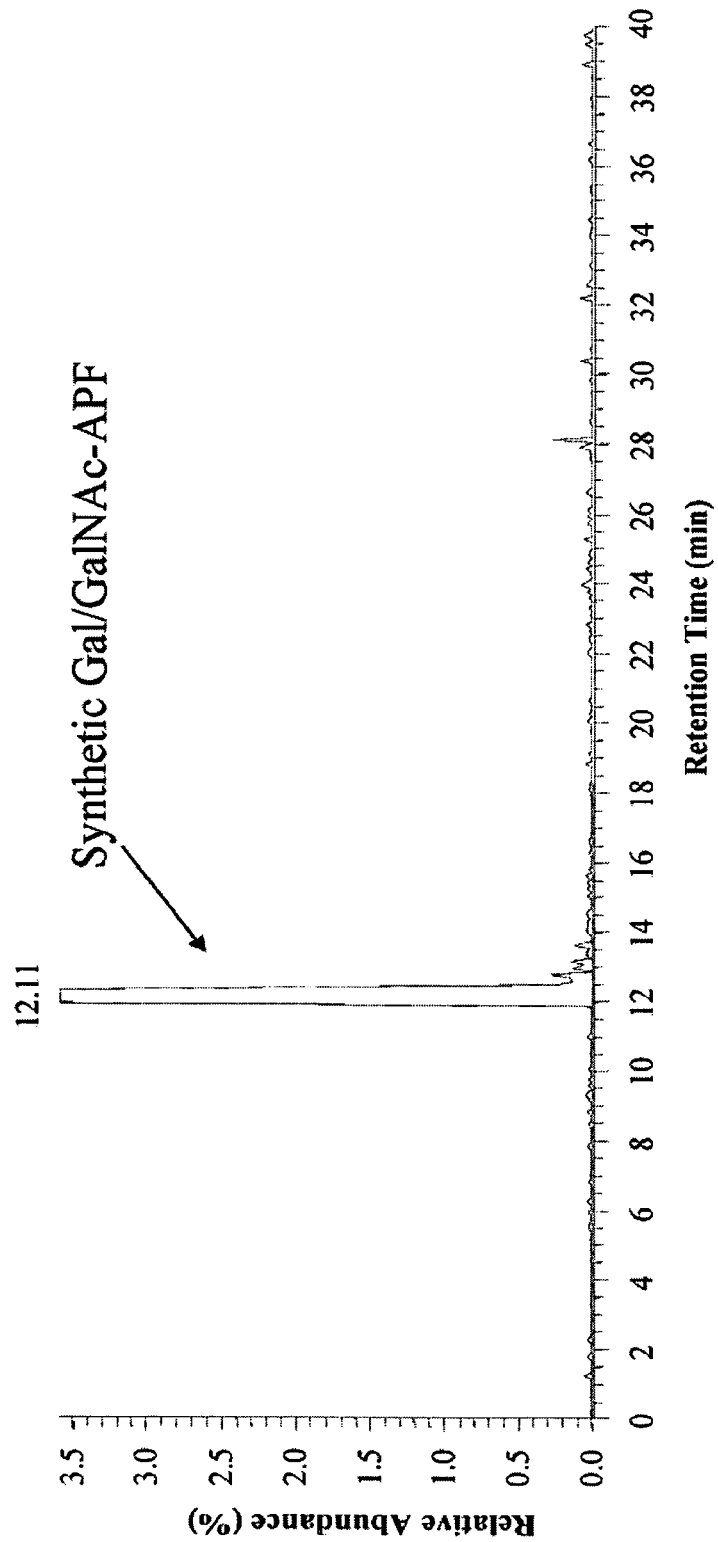

Native APF bound to wheat germ agglutinin and *Tritrichomonas mobilensis* lectins, but not to a variety of other lectins, confirming the likely presence of a terminal sialic acid residue. Treatment of native APF with a neuraminidase that cleaves sialic acid linked by any of four known linkages [2,3; 2,6; 2,8; or 2,9] did not decrease its biological activity, but did allow subsequent binding of APF to *Griffonia simplicifolia* I, peanut agglutinin, Jacalin lectin and *Erythrina cristagalli* with elution of biologically active toxin. These results indicate the possible presence of galactose and N-acetyllactosamine (galactose $\beta$1-4 N-acetylglucosamine), respectively. Apparent lack of binding of the desialylated APF to *Vicia* villosa lectin indicated that the disaccharide moiety remaining did not consist of galactos$\alpha$1-3N-acetylgalactosamine, and lack of binding to *Griffonia simplicifolia* II confirmed that the N-acetylglucosamine moiety was not terminal following removal of sialic acid. The sialic acid was subsequently proven to be linked via a 2,3 bond to the galactose moiety by demonstration of binding to *Griffonia simplicifolia* I and *Erythrina cristagalli* lectins after digestion with neuraminidase specific for 2,3 bond cleavage. The deduced structure of APF was therefore sialic acid 2,3 linked to either galactose β1-4 N-acetylglucosamine or galactose β1-3 N-acetylgalactosamine, which was in turn O-linked to threonine on the N-terminus of the peptide. Isoelectric focusing of the complete sialylated native APF indicated an acidic peptide with an isoelectric point of approximately 2.3.

EXAMPLE 4

Total Synthesis of APF

The invention encompasses any APF molecule having antiproliferative activity, particularly for bladder cells, comprising one or more sugar moieties and a hydrophobic moiety. Isolated natural APF molecules are encompassed in the invention, as are synthetic APF molecules. In particular, an APF molecule is synthesized by any suitable means in the art. In specific embodiments, however, the molecule is synthesized as described in this Example.

Because APF bound to *Erythrina cristagalli*, and because it is a secreted rather than membrane-bound peptide, synthesis started with a N-acetylglucosamine (GlcNAc) linked to threonine using both α and β-glycosylated amino acid building blocks for solid phase synthesis of the nonaglycopeptide. A chemoenzymatic approach was taken to construct the complete molecule via synthesis of appropriately Fmoc-protected N-acetyllactosamine-threonine glycoamino acids in both configurations. These were then incorporated into a peptide chain containing the other eight amino acids. Because it was known from the lectin binding studies that the sialic acid moiety was not necessary for APF activity, both α and β-N-acetyllactosamine modified peptides were then assayed for their antiproliferative activity as well as their ability to regulate specific growth factor production by explanted primary normal bladder epithelial cells.

Like native APF, the nonsialylated alpha anomer of the N-acetyllactosamine derivative was a potent inhibitor of cell proliferation, having an $IC_{50}$ of approximately 0.4 nM; maximal inhibition was possible using as little as 1 nM of the synthetic toxin (FIG. 2). In comparison, the beta anomer of the N-acetyllactosamine derivative and the nonglycosylated peptide had less measurable activity. The neuraminic acid unit was therefore then added to the alpha anomer using recombinant 2,3-sialyltransferase, and the antiproliferative activity of the sialylated derivative determined to be similar to the nonsialylated glycopeptide (FIG. 2). The same 1 nM concentration of sialylated or nonsialylated alpha anomeric synthetic APF that maximally inhibited 3H-thymidine incorporation was also shown to significantly decrease cell counts (data not shown), as well as significantly decrease HB-EGF production and increase EGF production by primary bladder cells (Table 3). APF as determined by all of these analyses was therefore an alpha anomeric sialoglycopeptide.

TABLE 3

Effect of Native APF vs. Synthetic APF and its Derivatives on Bladder Epithelial Cell Growth Factor Production

| | HB-EGF (ng/ml) | EGF (ng/ml) |
|---|---|---|
| Native APF | 0.18 ± 0.25* | 0.49 ± 0.14* |
| Mock APF | 5.24 ± 1.8 | 0.02 ± 0.02 |
| Synth APF (hexNAc/sial) | 0.13 ± 0.1† | 0.54 ± 0.12† |
| Synth APF (hexNAc) | 0.05 ± 0.1† | 0.38 ± 0.01† |
| Synth APF (peptide alone) | 4.65 ± 0.5 | 0.001 ± 0.002 |

*$p < 0.0001$ compared to Mock APF
†$p < 0.0001$ compared to Peptide alone

However, while a beta anomeric form of N-acetylglucosamine linked to threonine has been previously described in eucaryotic cells, the alpha anomeric form has not, whereas O-α-N-acetylgalactosamine is commonly found in modified eucaryotic cell proteins. Therefore APF was synthesized to include the alpha anomeric form of N-acetylgalactosamine linked β1->3 to galactose. As also shown in FIG. 2, this synthetic APF had activity similar to the synthetic compound comprising an alpha N-acetylglucosamine. Microcapillary LC-MS/MS in which desialylated native APF was spiked with either the GalNAc-containing or GlcNAc-containing synthetic glycopeptide (FIGS. 3A and 3B) was therefore used to establish the correct structure for APF. Both the native and synthetic GalNAc-containing APF derivatives had an identical retention time that was readily distinguishable from that of the GlcNAc-containing compound. The correct structure of APF is therefore the GalNAc-containing sialoglycopeptide shown in FIG. 4.

EXAMPLE 5

Inhibition of Bladder Cancer Cell Proliferation by Native and Synthetic APF

Figure 5:
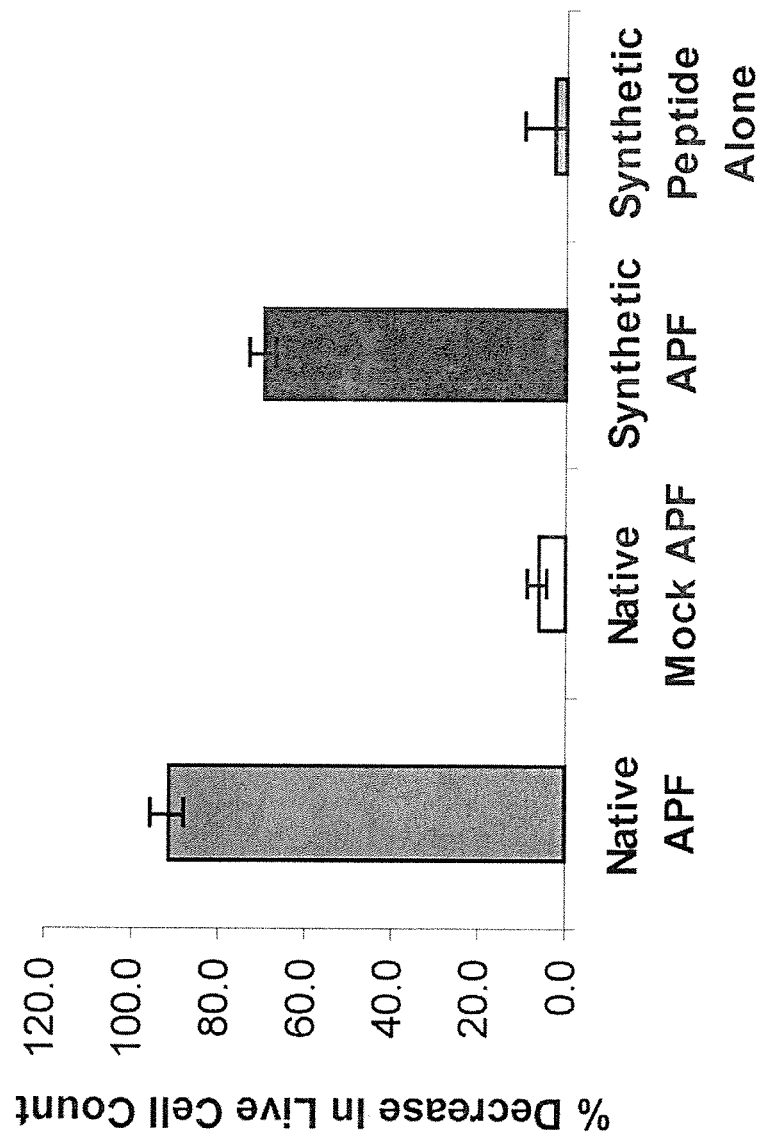
FIG. 5 shows inhibition of T24 cell proliferation by native and synthetic APF. Native APF (estimated concentration 3-5 μg/ml based on absorbance at 260 nm), an equivalent volume of Mock APF, synthetic GalGalNAc APF (3.0 μg/ml of glycopeptide), or an equimolar amount of peptide backbone alone were compared for their ability to inhibit cell proliferation by determining live cell count after 48 hours using trypan blue exclusion. All specimens were assayed in triplicate; data are expressed as the mean decrease in cell count, and vertical lines indicate standard error of the mean.

Additional evidence that the synthetic and native APF were the same was provided by measurement of their antiproliferative activities against a bladder carcinoma T24 cell line, using live cell count as determined by trypan blue exclusion. As shown in FIG. 5, these cells were sensitive to both native and synthetic APF species at approximately the same concentration.

EXAMPLE 6

Identification of APF mRNA by Northern Blot Analysis

Figure 6:
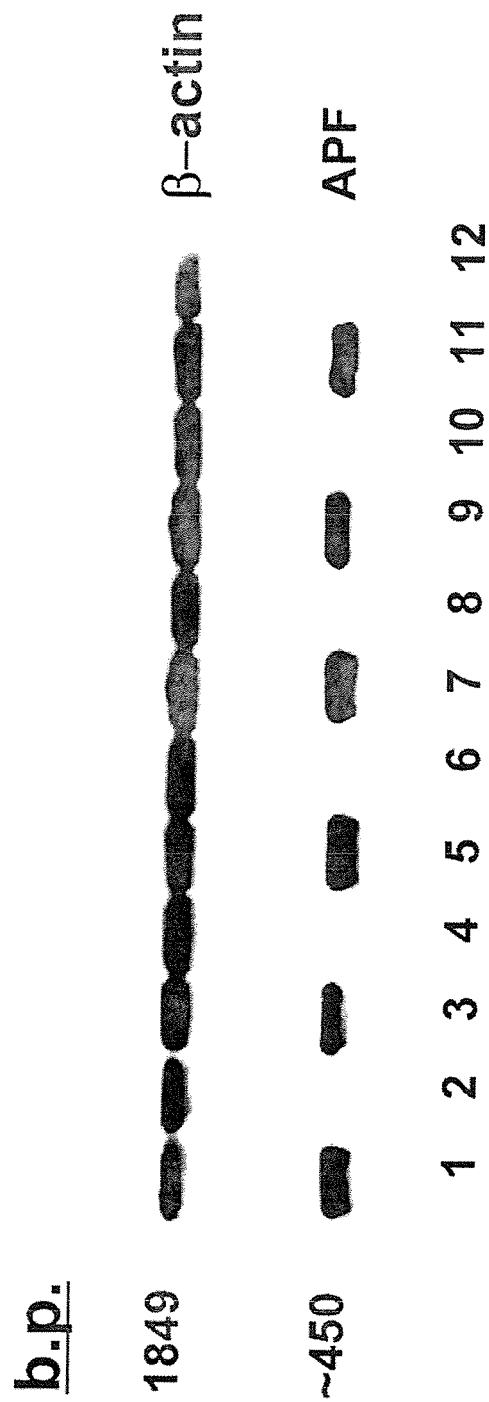
FIG. 6 provides Northern blot analysis of mRNA encoding the APF nonapeptide. Total RNA was extracted from explanted bladder epithelial cells from 6 patients with interstitial cystitis (lanes 1, 3, 5, 7, 9, and 11) and their age-, race-, and gender matched asymptomatic controls (lanes 2, 4, 6, 8, 10, and 12). The membrane was then incubated with DIG-labeled probes for APF mRNA and beta actin mRNA and developed using a chemiluminescent substrate.

Northern blot analysis of mRNA extracted from the explanted bladder epithelial cells of 6 IC patients and 6 normal controls was performed to provide additional evidence that APF was a frizzled 8-related peptide. As shown in FIG. 6, a small (approximately 450 b.p.) mRNA species that bound to a probe encoding the nonapeptide was present only in the extracts of all 6 cell explants from patients with IC previously shown to produce APF, but not in extracts of any explanted cells from age-, race- and gender-matched controls that did not produce APF. Although a faint band was also seen at approximately 3100 b.p. in IC but not control specimens on three of five experiments, it was not detectable in the other two experiments, and the predominant band was at 450 b.p. each time. However, no band was seen at the size of full length mRNA for human frizzled 8 (4 Kb), and no bands were seen for control cells in any experiment. In comparison, all cells from both groups appeared to produce similar amounts of beta actin mRNA.

EXAMPLE 7

Therapeutic Embodiments with Inhibitory Compounds for APF

In some aspects of the invention, it is beneficial to provide to an individual in need thereof an inhibitory compound for APF, thereby reducing partly or completely the anti-cell proliferation activity or production of APF. For example, for treating a bladder condition an inhibitor of APF is delivered to an individual suffering from at least one symptom of the bladder condition or to an individual suspected of having the bladder condition. In specific embodiments, the inhibitor of APF is an antibody that binds thereto, or a small molecule inhibitor of APF binding to its target. In other aspects, the inhibitor of APF is a compound that inhibits APF production, such as an antisense oligonucleotide or small interfering RNA, or any compound that could also inhibit APF production. In another aspect, the inhibitor of APF is a compound that stimulates the breakdown of APF.

The inhibitor of APF may be delivered to the individual by any suitable means. In specific embodiments of the present invention, the inhibitor of APF is comprised as an oral medication and/or is delivered via a catheter. A sufficient amount may be delivered directly to bladder tissue or it may be delivered systemically. A sufficient amount is one that ameliorates at least one symptom or finding (sign) of the bladder condition, and a skilled artisan recognizes standard methods to determine such an amount.

EXAMPLE 8

Therapeutic Embodiments with APF

Figure 8:
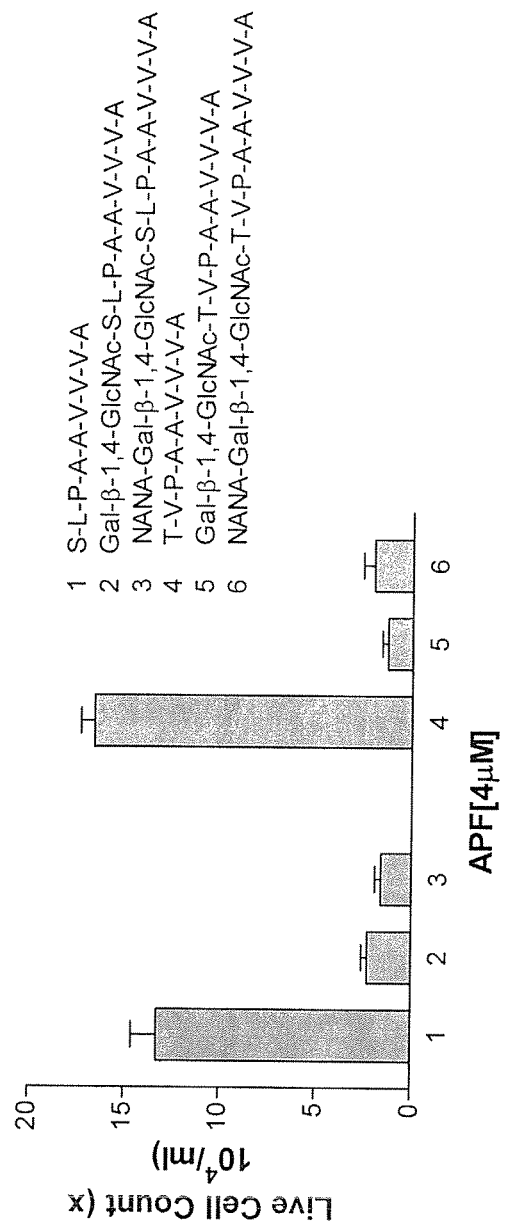
FIG. 8 demonstrates antiproliferative activity against normal human bladder epithelial cells of 2 different peptides (#1, corresponds to SEQ ID NO:5, and #4, corresponds to SEQ ID NO:1) and their sugar derivatives, having two (#2 and #5, each unsialyated (SEQ ID NO:29 and SEQ ID NO:31, respectively)) and three (#3 and #6 (SEQ ID NO:30 and SEQ ID NO:32, respectively)) sugar moieties.

In some aspects of the invention, it is beneficial to deliver to an individual in need thereof an APF composition to provide its anti-cell proliferation activity. For example, for treating bladder cancer an APF composition is delivered to an individual suffering from at least one symptom or finding (sign) of bladder cancer or to an individual suspected of having bladder cancer. FIG. 8 demonstrates antiproliferative activity against normal human bladder epithelial cells of 2 different peptides (#1, corresponds to SEQ ID NO:1, and #4, corresponds to SEQ ID NO:5) and their sugar derivatives, having two (#2 and #5, each unsialyated) and three (#3 and #6) sugar moieties.

Figure 9:
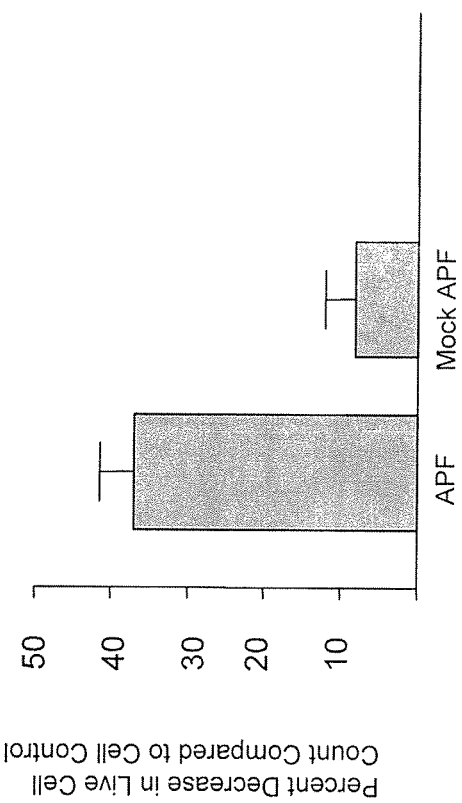
FIG. 9 shows APF inhibitory activity against LNCaP prostate cancer cells in vitro.

In other embodiments, prostate cancer cells (such as the exemplary LNCaP cells) are treated with APF compositions. LNCaP cells were plated at $2 \times 10^4$ cells per well of a 24 well tissue culture plate in DMEM medium containing 10% fetal bovine serum, 1% L-glutamine, 1% antibiotic/antimycotic solution, and grown at 37° C. in a 5% $CO_2$ atmosphere. The next day the medium was changed to DMEM containing the same additives except without fetal bovine serum, after which HPLC-purified APF or an equivalent amount of mock APF was added to each well. Live cell counts were performed on Day 3 of incubation by trypan blue exclusion. Values are the percent decrease in cell count compared to cell control given medium alone, and are given as the mean of triplicate wells; vertical lines are the standard deviation. The cells were sensitive to the antiproliferative activity of native purified APF (FIG. 9).

The APF composition may be delivered to the individual by any suitable means. In specific embodiments of the present invention, the APF composition is comprised as an oral medication and/or is delivered via a catheter, orally, intravenously, topically, subcutaneously, transcutaneously, intramuscularly, intra-jointly, parenterally, peritoneally, intranasally, intravesically, or by inhalation. A sufficient amount may be delivered directly to bladder tissue or it may be delivered systemically. A sufficient amount is one that ameliorates when given alone or in combination with other agents or other types of therapy at least one symptom or objective finding of the bladder cancer, and a skilled artisan recognizes standard methods to determine such an amount.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

PATENTS

U.S. Pat. No. 5,811,393
U.S. Pat. No. 5,916,871
U.S. Pat. No. 5,962,645
U.S. Pat. No. 6,156,522
U.S. Pat. No. 6,232,289
U.S. Pat. No. 6,376,197
U.S. Pat. No. 6,600,018

PUBLICATIONS

Ahn J M, Boyle N A, MacDonald M T, Janda K D Peptidomimetics and peptide backbone modifications. (2002) Mini Rev. Med. Chem., 2: 463-73

Aronov, O., Horowitz, A. T., Gabizon, A., Gibson, D. (2003) Bioconjug Chem 14(3):563-74.

Auger, G., Blanot, D., van Heijenoort, J., Nadal, C., Goumay, M. F., Winchenne, J. J., Boffa, G. A., Lambin, P., Maes, P., & Tartar, A. (1989) J Cell Biochem 40, 439-451.

Bafico, A., Gazit, A., Pramila, T., Finch, P. W., Yaniv, A., & Aaronson, S. A. (1999) J Biol Chem 274, 16180-16187.

Brensinger, C., Matthews, Y. L., Abele, S. T., Kusek, J. W., et al. (2001) Urology 57, 67-81.

Clugston P A, Vistnes M D, Perry L C, Maxwell G P, Fisher J (1995) Ann Plast Surg. Jan; 34(1):12-5.

Curhan, G. C., Speizer, F. E., Hunter, D. J., Curhan, S. G., & Stampfer, M. J. (1999) J Urol 161, 549-552.

Di Stefano, G., Tubaro, M., Lanza, M., Boga, C., Fiume, L., Traldi, P. Rapid Commun Mass Spectrom 17(22):2503-7.

Heath, T. D. & Martin, F. J. (1986) Chem Phys Lipids 40(2-4): 347-358.

Johansson, S. L. & Fall, M. (1990) J Urol 143, 1118-1124.

Jones, S. E., Jomarcy, C., Grist, J., Stewart, H. J., & Neal, M. J. (2000) Neuroreport 11, 3963-3967.

Jones, S. E., Jomacy, C. (2002) BioEssays 24, 811-820.

Keay, S., Zhang C—O, Shoenfelt J, Erickson D R, Whitmore K, Warren J W, Marvel R, & Chai T. (2001) Urology 57, 9-14.

Keay, S., Kleinberg, M., Zhang, C—O, Hise, M. K., & Warren, J. W. (2000) J Urol 64, 2112-2118.

Keay, S., Zhang, C-O., Shoenfelt, J. L., & Chai, T. C. (2003) Urology 61, 1278-1284.

Keay, S., Seillier-Moiseiwitsch, F., Zhang, C-O, Chai, T. C., & Zhang, J. (2003) Physiol Genomics 14, 107-115.

Keay, S., Zhang, C-O., Hise, M., Trifillis, A. L., Hebel, J. R., Jacobs, S. C., & Warren JW. (1996) J Urol 156, 2073-2078.

Keay, S., Zhang, C-O., Hise, M. K., Hebel, J. R., Jacobs, S. C., Gordon, D., Whitmore, K., Bodison, S., Gordon, N., & Warren, J. W. (1998) Urology 52, 974-978.

Leuck, M., & Kunz, H. (1997) J PraktChemie/Chemiker Zeitung 339, 322-334.

Mandler, R., Kobayashi, H., Hinson, E. R., Brechbiel, M. W., Waldmann, T. A. (2004) Cancer Res 64(4):1460-1467.

Moos, P. J., Fattaey, H. K., & Johnson, T. C. (1995) J Cell Biochem 59, 79-90.

Ou, X. H., Kuang, A. R., Peng, X., Zhong, Y. G. (2003) World J Gastroenterol 9(8):1675-8.

Pandur, P., Maurus, D., Kuhl, M. (2002) Bioessays 24, 881-884.

Polo M, Smith P D, Kim Y J, Wang X, Ko F, Robson M C (1999) Ann Plast Surg. August; 43(2):185-90.

Qiu, D., Gandhi, S. S., & Koganty, R. R. (1996) Tetrahedron Letters 37, 595-598. Safavy, A., Bonner, J. A., Waksal, H. W., Buchsbaum, D. J., Gillespie, G. Y., Khazaeli, M. B., Arani, R., Chen, D. T., Carpenter, M., Raisch, K. P. (2003) Bioconjug Chem 14(2):302-10.

Rashid, H. H., Reeder, J. E., O'Connell, M. J., Zhang, C.-O., Messing, E. M., and Keay, S. K. (2004) BMC Urology 4:3, 1-5.

Saitoh, T., Hirai, M., & Katoh, M. (2001) Int J Oncol 18, 991-996.

Schon, M. P. (1999) J Invest Dermatol. September; 113(3): 427.

Schumann, H., Holtz, J., Zerkowski, H. R., & Hatzfield, M. (2000) Cardiovasc Res 45, 720-728.

Sharifi, B. G. & Johnson, T. C. (1987) J Biol Chem 262, 15752-15755

Skoluda, D., Wegner, K., & Lemmel, E-M. (1974) Urologe 13, 15-23. Tomaszewski, J. E., Landis, J. R., Russack, V., Williams, T. M., Wang, L. P., Hardy, C., Svarovsky, S. A. &Barchi, J. J., Jr. (2003) Carbohydr Res 338, 1925-1935.

Thievessen, J., Seifert, H. H., Swiatkowski, S., Florl, A. R., & Schulz, W. A. (2003) Br J Cancer 88, 1932-1938.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A composition comprising a glycopeptide having one to six sugar moieties, wherein at least one sugar moiety is linked to
   a) a peptide moiety comprises SEQ ID NO:10; or
   b) a peptide moiety having one or two conservative substitutions in SEQ ID NO:10; or
   c) a peptide moiety comprising SEQ ID NO:10 except that the first and second N-terminal amino acids are serine and leucine, respectively.

2. The composition of claim 1, wherein one of the residues of the peptide is a linking amino acid that links the peptide to a sugar, and wherein the linking amino acid comprises a heteroatom covalently linked to one of the sugar moieties.

3. The composition of claim 2, wherein the linking amino acid is a serine, threonine, or cysteine.

4. The composition of claim 2, wherein the composition comprises two sugar residues and nine amino acids, wherein said linking amino acid is a serine, a threonine or a cysteine.

5. The composition of claim 1, wherein the linkage between the sugar and the peptide is in the alpha or beta configuration.

6. The composition of claim 1, wherein the linkage between the sugar and the peptide is in alpha configuration.

7. The composition of claim 1, wherein the peptide moiety of b) comprises the same sequence as SEQ ID NO:3, SEQ ID NO:4, or SEQ ID NO:6, except that the proline is a D-proline.

8. The composition of claim 1, wherein the conservative substitution comprises a hydrophobic conservative substitution.

9. The composition of claim 8, wherein the hydrophobic conservative substitution comprises a substitution at one or more alanines, one or more valines, a proline; or a combination thereof.

10. The composition of claim 1, wherein the composition comprises:
    (a) Sialic acid-galactose-Nacetylgalactosamine-threonine-valine-D-proline-alanine-alanine-valine-valine-v aline-alanine;
    (b) Sialic acid-galacto se-Nacetylglucosamine-threonine-valine -D-proline- alanine-alanine-valine -valine-valine-alanine; or
    (c) Sialic acid-galactose-Nacetylglucosamine- serine-leucine-D-proline-alanine-alanine-valine -valine-valine-alanine.

11. The composition of (a) in claim 10, further defined as having one or more of the following:
    the sialic acid is linked to galactose via a 2,3 linkage;
    the galactose is linked to the N-acetylgalactosamine via a 1,3 linkage; or
    the N-acetyl galactosamine is linked to threonine via an 0 linkage in an alpha configuration.

12. The composition of (b) in claim 10, further defined as having one or more of the following:
    the sialic acid is linked to galactose via a 2,3 linkage; the galactose is linked to the N-acetylglucosamine via a 1,4 linkage; or the N-acetyl glucosamine is linked to threonine via an 0 linkage in an alpha configuration.

13. The composition of (c) in claim 10, further defined as having one or more of the following:
    the sialic acid is linked to galactose via a 2,3 linkage;
    the galactose is linked to the N-acetylglucosamine via a 1,4 linkage; or
    the N-acetylglucosamine is linked to serine via an 0 linkage in an alpha configuration.

14. The composition of claim 1, further comprising a delivery vehicle.

15. The composition of claim 14, wherein the delivery vehicle is a liposome, a cell, a conjugated molecule, a nanoparticle, or a mixture thereof.

16. The composition of claim 15, wherein the conjugated molecule comprises an antibody, a peptide, folate, polyethylene glycol, a drug, a liposome, or lactosaminated human albumin.

17. The composition of claim 15, wherein the nanoparticle comprises colloidal gold.

18. The composition of claim 1 comprised in a pharmaceutically acceptable excipient.

19. A composition comprising a glycopeptide, wherein the glycopeptide comprises two sugars and a peptide that comprises SEQ ID NO:10, wherein the sugars are β-galactose and N-acetyl galactosamine, wherein the N-acetyl galactosamine is linked to the peptide in the alpha configuration.

20. A kit, comprising the composition of claim 1, wherein the composition is housed in a suitable container.

21. The composition of claim 1, wherein the peptide comprises an amino acid mimetic.

22. The composition of claim 21, wherein the amino acid mimetic is a mimetic of threonine, valine, alanine, serine, or leucine.

23. The composition of claim 19, wherein the peptide comprises an amino acid mimetic.

24. The composition of claim 23, wherein the amino acid mimetic is a mimetic of threonine, valine, alanine, serine, or leucine.

25. The kit of claim 20, wherein the peptide comprises an amino acid mimetic.

26. The kit of claim 25, wherein the amino acid mimetic is a mimetic of threonine, valine, alanine, serine, or leucine.

\* \* \* \* \*

UNITED STATES PATENT AND TRADEMARK OFFICE
CERTIFICATE OF CORRECTION

| | |
|---|---|
| PATENT NO. | : 9,085,604 B2 |
| APPLICATION NO. | : 11/955755 |
| DATED | : July 21, 2015 |
| INVENTOR(S) | : Susan K. Keay et al. |

It is certified that error appears in the above-identified patent and that said Letters Patent is hereby corrected as shown below:

Column 1, lines 6-11, delete first paragraph and insert --This invention was made with government support under Grant Number DK052596 awarded by The National Institutes of Health. The government has certain rights in the invention.--

Signed and Sealed this
Twenty-third Day of February, 2016

Michelle K. Lee
*Director of the United States Patent and Trademark Office*

UNITED STATES PATENT AND TRADEMARK OFFICE
CERTIFICATE OF CORRECTION

PATENT NO. : 9,085,604 B2  
APPLICATION NO. : 11/955755  
DATED : July 21, 2015  
INVENTOR(S) : Susan K. Keay et al.

Page 1 of 1

It is certified that error appears in the above-identified patent and that said Letters Patent is hereby corrected as shown below:

Column 1, lines 6-11, delete first paragraph and insert --This invention was made with government support under Grant Numbers DK052596 and DK044818 awarded by The National Institutes of Health. The government has certain rights in the invention.--

This certificate supersedes the Certificate of Correction issued February 23, 2016.

Signed and Sealed this  
Twenty-sixth Day of July, 2016

Michelle K. Lee  
*Director of the United States Patent and Trademark Office*

SEQUENCE LISTING

<160> NUMBER OF SEQ ID NOS: 32

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 1

Thr Val Pro Ala Ala Val Val Val Ala
1               5

<210> SEQ ID NO 2
<211> LENGTH: 27
<212> TYPE: DNA
<213> ORGANISM: Artificial Sequence
<220> FEATURE:
<223> OTHER INFORMATION: Synthetic Primer

<400> SEQUENCE: 2
accgtgcccg ccgcggtggt ggtcgcc                                              27

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Ser Val Pro Ala Ala Val Val Val Ala
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Thr Val Pro Ala Ala Val Val Leu Ala
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Ser Leu Pro Ala Ala Val Val Val Ala
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Cys Thr Val Pro Ala Ala Val Val Val Ala
1               5                   10

<210> SEQ ID NO 7
<211> LENGTH: 694
<212> TYPE: PRT
<213> ORGANISM: Homo sapiens

<400> SEQUENCE: 7

Met Glu Trp Gly Tyr Leu Leu Glu Val Thr Ser Leu Leu Ala Ala Leu
1               5                   10                  15
```

```
Ala Leu Leu Gln Arg Ser Ser Gly Ala Ala Ala Ser Ala Lys Glu
             20                  25                  30

Leu Ala Cys Gln Glu Ile Thr Val Pro Leu Cys Lys Gly Ile Gly Tyr
         35                  40                  45

Asn Tyr Thr Tyr Met Pro Asn Gln Phe Asn His Asp Thr Gln Asp Glu
 50                  55                  60

Ala Gly Leu Glu Val His Gln Phe Trp Pro Leu Val Glu Ile Gln Cys
 65              70                  75                  80

Ser Pro Asp Leu Lys Phe Phe Leu Cys Ser Met Tyr Thr Pro Ile Cys
                 85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
             115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
             180                 185                 190

Arg Gly Gly Gly Arg Gly Gly Gly Gly Asp Ala Ala Pro Pro
         195                 200                 205

Ala Arg Gly Gly Gly Gly Gly Lys Ala Arg Pro Pro Gly Gly Gly
     210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
             260                 265                 270

Glu Arg Ala Phe Thr Val Phe Trp Ile Gly Leu Trp Ser Val Leu Cys
         275                 280                 285

Phe Val Ser Thr Phe Ala Thr Val Ser Thr Phe Leu Ile Asp Met Glu
290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
             340                 345                 350

Ala Gly Gly Ala Ala Ala Gly Ala Gly Ala Gly Ala Gly Ala Gly
         355                 360                 365

Gly Pro Gly Gly Arg Gly Glu Tyr Glu Glu Leu Gly Ala Val Glu Gln
370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
             420                 425                 430
```

```
Ala Ile Ala Gly Tyr Ser Gln Tyr Phe His Leu Ala Ala Trp Leu Val
            435                 440                 445

Pro Ser Val Lys Ser Ile Ala Val Leu Ala Leu Ser Ser Val Asp Gly
        450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
                485                 490                 495

Thr Met Phe Leu Leu Ala Gly Phe Val Ser Leu Phe Arg Ile Arg Ser
            500                 505                 510

Val Ile Lys Gln Gln Asp Gly Pro Thr Lys Thr His Lys Leu Glu Lys
        515                 520                 525

Leu Met Ile Arg Leu Gly Leu Phe Thr Val Leu Tyr Thr Val Pro Ala
    530                 535                 540

Ala Val Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
                565                 570                 575

Gln Ala Arg Arg Pro Asp Tyr Ala Val Phe Met Leu Lys Tyr Phe Met
            580                 585                 590

Cys Leu Val Val Gly Ile Thr Ser Gly Val Trp Val Trp Ser Gly Lys
        595                 600                 605

Thr Leu Glu Ser Trp Arg Ser Leu Cys Thr Arg Cys Cys Trp Ala Ser
    610                 615                 620

Lys Gly Ala Ala Val Gly Gly Ala Gly Thr Ala Ala Gly Gly
625                 630                 635                 640

Gly Gly Gly Pro Gly Gly Gly Gly Gly Pro Gly Gly Gly
                645                 650                 655

Gly Pro Gly Gly Gly Gly Ser Leu Tyr Ser Asp Val Ser Thr Gly
            660                 665                 670

Leu Thr Trp Arg Ser Gly Thr Ala Ser Ser Val Ser Tyr Pro Lys Gln
    675                 680                 685

Met Pro Leu Ser Gln Val
    690

<210> SEQ ID NO 8
<211> LENGTH: 3195
<212> TYPE: DNA
<213> ORGANISM: Homo sapiens

<400> SEQUENCE: 8
acagcatgga gtggggttac ctgttggaag tgacctcgct gctggccgcc ttggcgctgc      60
tgcagcgctc tagcggcgct gcggccgcct cggccaagga gctggcatgc caagagatca     120
ccgtgccgct gtgtaagggc atcggctaca actacaccta catgcccaat cagttcaacc     180
acgacacgca agacgaggcg ggcctggagg tgcaccagtt ctggccgctg gtggagatcc     240
agtgctcgcc cgatctcaag ttcttcctgt gcagcatgta cacgcccatc tgcctagagg     300
actacaagaa gccgctgccg ccctgccgct cggtgtgcga gcgcgccaag gccggctgcg     360
cgccgctcat gcgccagtac ggcttcgcct ggccagaccg catgcgctgc gaccggctgc     420
ccgagcaagg caaccctgac acgctgtgca tggactacaa ccgcaccgac ctaaccaccg     480
ccgcgcccag cccgccgcgc cgcctgccgc cgccgccgcc cggcgagcag ccgccttcgg     540
gcagcggcca cggccgcccg ccgggggcca ggccccccgca ccgcggaggc ggcaggggcg     600
```

-continued

```
gtggcggcgg ggacgcggcg gcgccccag ctcgcggcgg cggcggtggc gggaaggcgc    660
ggccccctgg cggcggcgcg gctccctgcg agcccgggtg ccagtgccgc gcgcctatgg    720
tgagcgtgtc cagcgagcgc cacccgctct acaaccgcgt caagacaggc cagatcgcta    780
actgcgcgct gccctgccac aaccccttt tcagccagga cgagcgcgcc ttcaccgtct    840
tctggatcgg cctgtggtcg gtgctctgct tcgtgtccac cttcgccacc gtctccacct    900
tccttatcga catggagcgc ttcaagtacc cggagcggcc cattatcttc ctctcggcct    960
gctacctctt cgtgtcggtg ggctacctag tgcgcctggt ggcgggccac gagaaggtgg   1020
cgtgcagcgg tggcgcgccg ggcgcggggg cgctggggg cgcgggcggc gcggcggcgg   1080
gcgcgggcgc ggcgggcgcg ggcgcgggcg gcccgggcgg gcgcggcgag tacgaggagc   1140
tgggcgcggt ggagcagcac gtgcgctacg agaccaccgg ccccgcgctg tgcaccgtgg   1200
tcttcttgct ggtctacttc ttcggcatgg ccagctccat ctggtgggtg atcttgtcgc   1260
tcacatggtt cctggcggcc ggtatgaagt ggggcaacga agccatcgcc ggctactcgc   1320
agtacttcca cctggccgcg tggcttgtgc ccagcgtcaa gtccatcgcg gtgctggcgc   1380
tcagctcggt ggacgcgac ccggtggcgg gcatctgcta cgtgggcaac cagagcctgg   1440
acaacctgcg cggcttcgtg ctggcgccgc tggtcatcta cctcttcatc ggcaccatgt   1500
tcctgctggc cggcttcgtg tccctgttcc gcatccgctc ggtcatcaag caacaggacg   1560
gccccaccaa gacgcacaag ctggagaagc tgatgatccg cctgggcctg ttcaccgtgc   1620
tctacaccgt gcccgccgcg gtggtggtcg cctgcctctt ctacgagcag cacaaccgcc   1680 gcgctggga ggcacgcac aactgcccgt gcctgcggga cctgcagccc gaccaggcac   1740
gcaggcccga ctacgccgtc ttcatgctca agtacttcat gtgcctagtg gtgggcatca   1800
cctcgggcgt gtgggtctgg tccggcaaga cgctggagtc ctggcgctcc ctgtgcaccc   1860
gctgctgctg ggccagcaag ggcgccgcgg tgggcggggg cgcgggcgcc acggccgcgg   1920
ggggtggcgc cggggccgggg ggcggcgcg cggggggacc cggcggcggc gggggccgg   1980 gcggcggcgg gggctccctc tacagcgacg tcagcactgg cctgacgtgg cggtcgggca   2040
cggcgagctc cgtgtcttat ccaaagcaga tgccattgtc ccaggtctga gcggagggga   2100
gggggcgccc aggaggggtg gggagggggg cgaggagacc caagtgcagc gaagggacac   2160
ttgatgggct gaggttccca cccccttcaca gtgttgattg ctattagcat gataatgaac   2220
tcttaatggt atccattagc tgggacttaa atgactcact tagaacaaag tacctggcat   2280
tgaagcctcc cagacccagc ccctttcct ccattgatgt gcgggagct cctcccgcca   2340 cgcgttaatt tctgttggct gaggaggggtg gactctgcgg cgtttccaga acccgagatt   2400
tggagccctc cctggctgca cttggctggg tttgcagtca gatacacaga tttcacctgg   2460
gagaacctct ttttctccct cgactcttcc tacgtaaact cccacccctg acttaccctg   2520 gaggagggg gaccgccacc tgatgggatt gcacggtttg ggtattctta atgaccaggc   2580
aaatgcctta agtaaacaaa caagaaatgt cttaattata caccccacgt aaatacgggt   2640
ttcttacatt agaggatgta tttatataat tatttgttaa attgtaaaaa aaaaagtgt   2700 aaatatgta tatatccaaa gatatagtgt gtacattttt ttgtaaaaag tttagaggct   2760 taccctgta agaacagata taagtattct attttgtcaa taaatgact tttgataaat   2820 gatttaacca ttgccctctc cccgcctct tctgagctgt cacctttaaa gtgcttgcta   2880
aggacgcatg gggaaaatgg acattttctg gcttgtcatt ctgtacactg accttaggca   2940
tggagaaaat tacttgttaa actctagttc ttaagttgtt agccaagtaa atatcattgt   3000
```

```
tgaactgaaa tcaaaattga gttttttgcac cttccccaaa gacggtgttt ttcatgggag    3060 ctctttctg  atccatggat aacaactctc actttagtgg atgtaaatgg aacttctgca    3120
aggcagtaat tccccttagg ccttgttatt tatcctgcat ggtatcacta aaggtttcaa    3180
aaccctgaaa aaaaa                                                     3195
```

```
<210> SEQ ID NO 9
<211> LENGTH: 685
<212> TYPE: PRT
<213> ORGANISM: Mus musculus

<400> SEQUENCE: 9

Met Glu Trp Gly Tyr Leu Leu Glu Val Thr Ser Leu Leu Ala Ala Leu
1               5                   10                  15

Ala Val Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Pro Gly Glu Gln
                165                 170                 175

Pro Pro Ser Gly Ser Gly His Ser Arg Pro Pro Gly Ala Arg Pro Pro
            180                 185                 190

His Arg Gly Gly Ser Ser Arg Gly Ser Gly Asp Ala Ala Ala Pro
        195                 200                 205

Pro Ser Arg Gly Gly Lys Ala Arg Pro Pro Gly Gly Gly Ala Ala Pro
    210                 215                 220

Cys Glu Pro Gly Cys Gln Cys Arg Ala Pro Met Val Ser Val Ser Ser
225                 230                 235                 240

Glu Arg His Pro Leu Tyr Asn Arg Val Lys Thr Gly Gln Ile Ala Asn
                245                 250                 255

Cys Ala Leu Pro Cys His Asn Pro Phe Phe Ser Gln Asp Glu Arg Ala
            260                 265                 270

Phe Thr Val Phe Trp Ile Gly Leu Trp Ser Val Leu Cys Phe Val Ser
        275                 280                 285

Thr Phe Ala Thr Val Ser Thr Phe Leu Ile Asp Met Glu Arg Phe Lys
    290                 295                 300

Tyr Pro Glu Arg Pro Ile Ile Phe Leu Ser Ala Cys Tyr Leu Phe Val
305                 310                 315                 320

Ser Val Gly Tyr Leu Val Arg Leu Val Ala Gly His Glu Lys Val Ala
                325                 330                 335
```

```
Cys Ser Gly Gly Ala Pro Gly Ala Gly Gly Arg Gly Gly Ala Gly Gly
            340                 345                 350

Ala Ala Ala Ala Gly Ala Gly Ala Ala Gly Arg Gly Ala Ser Ser Pro
        355                 360                 365

Gly Ala Arg Gly Glu Tyr Glu Glu Leu Gly Ala Val Glu Gln His Val
370                 375                 380

Arg Tyr Glu Thr Thr Gly Pro Ala Leu Cys Thr Val Phe Leu Leu
385                 390                 395                 400

Val Tyr Phe Phe Gly Met Ala Ser Ser Ile Trp Val Ile Leu Ser
                405                 410                 415

Leu Thr Trp Phe Leu Ala Ala Gly Met Lys Trp Gly Asn Glu Ala Ile
            420                 425                 430

Ala Gly Tyr Ser Gln Tyr Phe His Leu Ala Ala Trp Leu Val Pro Ser
        435                 440                 445

Val Lys Ser Ile Ala Val Leu Ala Leu Ser Ser Val Asp Gly Asp Pro
450                 455                 460

Val Ala Gly Ile Cys Tyr Val Gly Asn Gln Ser Leu Asp Asn Leu Arg
465                 470                 475                 480

Gly Phe Val Leu Ala Pro Leu Val Ile Tyr Leu Phe Ile Gly Thr Met
                485                 490                 495

Phe Leu Leu Ala Gly Phe Val Ser Leu Phe Arg Ile Arg Ser Val Ile
            500                 505                 510

Lys Gln Gln Gly Gly Pro Thr Lys Thr His Lys Leu Glu Lys Leu Met
        515                 520                 525

Ile Arg Leu Gly Leu Phe Thr Val Leu Tyr Thr Val Pro Ala Ala Val
530                 535                 540

Val Val Ala Cys Leu Phe Tyr Glu Gln His Asn Arg Pro Arg Trp Glu
545                 550                 555                 560

Ala Thr His Asn Cys Pro Cys Leu Arg Asp Leu Gln Pro Asp Gln Ala
                565                 570                 575

Arg Arg Pro Asp Tyr Ala Val Phe Met Leu Lys Tyr Phe Met Cys Leu
            580                 585                 590

Val Val Gly Ile Thr Ser Gly Val Trp Val Trp Ser Gly Lys Thr Leu
        595                 600                 605

Glu Ser Trp Arg Ala Leu Cys Thr Arg Cys Cys Trp Ala Ser Lys Gly
610                 615                 620

Ala Ala Val Gly Ala Gly Ala Gly Gly Ser Gly Pro Gly Gly Ser Gly
625                 630                 635                 640

Pro Gly Pro Gly Gly Gly Gly His Gly Gly Gly Gly Ser Leu
                645                 650                 655

Tyr Ser Asp Val Ser Thr Gly Leu Thr Trp Arg Ser Gly Thr Ala Ser
            660                 665                 670

Ser Val Ser Tyr Pro Lys Gln Met Pro Leu Ser Gln Val
        675                 680                 685

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-Proline
```

```
<400> SEQUENCE: 10

Thr Val Pro Ala Ala Val Val Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylgalactosamine

<400> SEQUENCE: 11

Thr Val Pro Ala Ala Val Val Ala
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylgalactosamine

<400> SEQUENCE: 12

Ser Val Pro Ala Ala Val Val Ala
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylgalactosamine

<400> SEQUENCE: 13

Thr Val Pro Ala Ala Val Val Leu Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylgalactosamine

<400> SEQUENCE: 14

Ser Leu Pro Ala Ala Val Val Val Ala
1               5

<210> SEQ ID NO 15
<211> LENGTH: 9
<212> TYPE: PRT
<213> ORGANISM: Artificial Sequence
<220> FEATURE:
```

<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylglucosamine

<400> SEQUENCE: 15

Thr Val Pro Ala Ala Val Val Val Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylglucosamine

<400> SEQUENCE: 16

Ser Val Pro Ala Ala Val Val Val Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylglucosamine

<400> SEQUENCE: 17

Thr Val Pro Ala Ala Val Val Leu Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetylglucosamine

<400> SEQUENCE: 18

Ser Leu Pro Ala Ala Val Val Val Ala
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Glycosylated threonine

<400> SEQUENCE: 19

Thr Val Pro Ala Ala Val Val Val Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Glycosylated serine

<400> SEQUENCE: 20

Ser Val Pro Ala Ala Val Val Val Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Glycosylated threonine

<400> SEQUENCE: 21

Thr Val Pro Ala Ala Val Val Leu Ala
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Glycosylated serine

<400> SEQUENCE: 22

Ser Leu Pro Ala Ala Val Val Val Ala
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Glycosylated cysteine

<400> SEQUENCE: 23

Cys Thr Val Pro Ala Ala Val Val Val Ala
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Gal-beta1-4GlcNAc-alpha -continued

```
<400> SEQUENCE: 24

Thr Val Pro Ala Ala Val Val Val Ala
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Gal-beta1-3GalNAc-alpha

<400> SEQUENCE: 25

Thr Val Pro Ala Ala Val Val Val Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Sialic acid-galactose-N-acetylgalactosamine

<400> SEQUENCE: 26

Thr Val Pro Ala Ala Val Val Val Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Sialic acid-galactose-N-acetylglucosamine

<400> SEQUENCE: 27

Thr Val Pro Ala Ala Val Val Val Ala
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Sialic acid-galactose-N-acetylglucosamine

<400> SEQUENCE: 28

Ser Leu Pro Ala Ala Val Val Val Ala
1               5

<210> SEQ ID NO 29
<211> LENGTH: 9
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified with unsialylated Gal-beta-1,4-GlcNAc

<400> SEQUENCE: 29

Ser Leu Pro Ala Ala Val Val Val Ala
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified with N-acetylneuraminic
      acid-Gal-beta-1,4-GlcNAc

<400> SEQUENCE: 30

Ser Leu Pro Ala Ala Val Val Val Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified with unsialylated Gal-beta-1,4-GlcNAc

<400> SEQUENCE: 31

Thr Val Pro Ala Ala Val Val Val Ala
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified with N-acetylneuraminic
      acid-Gal-beta-1,4-GlcNAc

<400> SEQUENCE: 32

Thr Val Pro Ala Ala Val Val Val Ala
1               5
```